(12) United States Patent
Lim

(10) Patent No.: US 12,171,789 B2
(45) Date of Patent: Dec. 24, 2024

(54) IMMUNOLOGICAL EXTRACT AND METHOD OF PRODUCTION

(71) Applicant: Kah Meng Lim, Singapore (SG)

(72) Inventor: Kah Meng Lim, Singapore (SG)

( * ) Notice: Subject to any disclaimer, the term of this patent is extended or adjusted under 35 U.S.C. 154(b) by 703 days.

(21) Appl. No.: 17/046,649

(22) PCT Filed: Apr. 10, 2019

(86) PCT No.: PCT/SG2019/050200
§ 371 (c)(1),
(2) Date: Oct. 9, 2020

(87) PCT Pub. No.: WO2019/199232
PCT Pub. Date: Oct. 17, 2019

(65) Prior Publication Data
US 2021/0361720 A1    Nov. 25, 2021

(30) Foreign Application Priority Data
Apr. 10, 2018  (SG) .......................... 10201802979V

(51) Int. Cl.
*A61K 35/57*     (2015.01)
*A61K 47/36*     (2006.01)
*A61K 47/42*     (2017.01)

(52) U.S. Cl.
CPC .............. *A61K 35/57* (2013.01); *A61K 47/36* (2013.01); *A61K 47/42* (2013.01)

(58) Field of Classification Search
CPC ..................................................... A61K 35/57
See application file for complete search history.

(56) References Cited

FOREIGN PATENT DOCUMENTS

| CN | 106235303 A | * 12/2016 |
| CN | 107868808 A | 4/2018 |
| WO | 2017012088 A1 | 1/2017 |
| WO | 2017155471 A1 | 9/2017 |

OTHER PUBLICATIONS

Ma et al, Sketch of the edible bird's nest and its important bioactivities. Food Research International (2012), 48(2), 559-567 (Year: 2012).*
Marcone, Characterization of the edible bird's nest the "Caviar of the East". Food research international (2005), vol. 38, No. 10, pp. 1125-1134 (Year: 2005).*
Zhang et al, In vitro bioaccessibility and antioxidant properties of edible bird's nest following simulated human gastro-intestinal digestion. BMC complementary and alternative medicine, (Dec. 5, 2014) vol. 14, pp. 468 (Year: 2014).*
Communication (International Search Report) issued by the International Searching Authority in International Application No. PCT/SG2019/050200 dated Jul. 31, 2019, 5 pages total.
Communication (Written Opinion) issued by the International Searching Authority in International Application No. PCT/SG2019/050200 dated Jul. 31, 2019, 6 pages total.
Parikh, A. et al., "A Review on Applications of Maltodextrin in Pharmaceutical Industry" International Journal of Pharmacy and Biological Sciences (2014) vol. 4, Issue 4, pp. 67-74.
Quek, M.C. et al., "Characterization of Edible Bird's Nest of Different Production, Species and Geographical Origins Using Nutritional Composition, Physicochemical Properties and Antioxidant Activities" Food Research International (2018) vol. 109, pp. 35-43.
Roh, K.B. et al. "Mechanisms of Edible Bird's Nest Extract-Induced Proliferation of Human Adipose-Derived Stem Cells" Evidence-Based Complementary Alternative Medicine (2012) vol. 2012, Article ID 797520, 11 pages total.
Runckel, C.W., "A Bird in the Hand" Business in Asia <URL: https://web.archive.org/web/20160218140252/http://www.business-in-asia.com/industries/birdnest_ for_ health.html> 6 pages total.
Yida, Z. et al., "Edible Bird's Nest Attenuates High Fat Diet-Induced Oxidative Stress and Inflammation via Regulation of Hepatic Antioxidant and Inflammatory Genes" BMC Complementary Alternative Medicine (2015) vol. 15, No. 310, 7 pages total.

* cited by examiner

*Primary Examiner* — Qiuwen Mi
(74) *Attorney, Agent, or Firm* — Troutman Pepper Hamilton Sanders LLP

(57) ABSTRACT

The present invention relates to a method of preparing an extract from edible bird's nest, a bird's nest extract and uses of the bird's nest extract. The method comprises preparing an edible bird's nest (EBN) mixture; and contacting the mixture with an extraction solution to bind a molecule in the mixture, wherein the extraction solution comprises at least one binding moiety selected from the group comprising an opsonin binding moiety, a complement protein binding moiety, a lectin binding moiety, a ficolin binding moiety, a collectin binding moiety, and a pentraxin binding moiety.

17 Claims, 6 Drawing Sheets
Specification includes a Sequence Listing.

SEQUENCE LISTING

```
<160> NUMBER OF SEQ ID NOS: 6

<210> SEQ ID NO 1
<211> LENGTH: 2413
<212> TYPE: PRT
<213> ORGANISM: Homo sapiens

<400> SEQUENCE: 1

Met Gly Ile Ser Thr Val Ile Leu Glu Met Cys Leu Leu Trp Gly Gln
1               5                   10                  15

Val Leu Ser Thr Gly Gly Trp Ile Pro Arg Thr Thr Asp Tyr Ala Ser
            20                  25                  30

Leu Ile Pro Ser Glu Val Pro Leu Asp Gln Thr Val Ala Glu Gly Ser
        35                  40                  45

Pro Phe Pro Ser Glu Ser Thr Leu Glu Ser Thr Ala Ala Glu Gly Ser
    50                  55                  60

Pro Ile Ser Leu Glu Ser Thr Leu Glu Ser Thr Val Ala Glu Gly Ser
65                  70                  75                  80

Leu Ile Pro Ser Glu Ser Thr Leu Glu Ser Thr Val Ala Glu Gly Ser
                85                  90                  95

Asp Ser Gly Leu Ala Leu Arg Leu Val Asn Gly Asp Gly Arg Cys Gln
            100                 105                 110

Gly Arg Val Glu Ile Leu Tyr Arg Gly Ser Trp Gly Thr Val Cys Asp
        115                 120                 125

Asp Ser Trp Asp Thr Asn Asp Ala Asn Val Val Cys Arg Gln Leu Gly
    130                 135                 140

Cys Gly Trp Ala Met Ser Ala Pro Gly Asn Ala Trp Phe Gly Gln Gly
145                 150                 155                 160

Ser Gly Pro Ile Ala Leu Asp Asp Val Arg Cys Ser Gly His Glu Ser
                165                 170                 175

Tyr Leu Trp Ser Cys Pro His Asn Gly Trp Leu Ser His Asn Cys Gly
            180                 185                 190

His Gly Glu Asp Ala Gly Val Ile Cys Ser Ala Ala Gln Pro Gln Ser
        195                 200                 205

Thr Leu Arg Pro Glu Ser Trp Pro Val Arg Ile Ser Pro Pro Val Pro
    210                 215                 220

Thr Glu Gly Ser Glu Ser Ser Leu Ala Leu Arg Leu Val Asn Gly Gly
225                 230                 235                 240
```

```
Asp Arg Cys Arg Gly Arg Val Glu Val Leu Tyr Arg Gly Ser Trp Gly
            245                 250                 255

Thr Val Cys Asp Asp Tyr Trp Asp Thr Asn Asp Ala Asn Val Val Cys
        260                 265                 270

Arg Gln Leu Gly Cys Gly Trp Ala Met Ser Ala Pro Gly Asn Ala Gln
    275                 280                 285

Phe Gly Gln Gly Ser Gly Pro Ile Val Leu Asp Val Arg Cys Ser
290                 295                 300

Gly His Glu Ser Tyr Leu Trp Ser Cys Pro His Asn Gly Trp Leu Thr
305                 310                 315                 320

His Asn Cys Gly His Ser Glu Asp Ala Gly Val Ile Cys Ser Ala Pro
                325                 330                 335

Gln Ser Arg Pro Thr Pro Ser Pro Asp Thr Trp Pro Thr Ser His Ala
            340                 345                 350

Ser Thr Ala Gly Pro Glu Ser Ser Leu Ala Leu Arg Leu Val Asn Gly
        355                 360                 365

Gly Asp Arg Cys Gln Gly Arg Val Glu Val Leu Tyr Arg Gly Ser Trp
    370                 375                 380

Gly Thr Val Cys Asp Asp Ser Trp Asp Thr Ser Asp Ala Asn Val Val
385                 390                 395                 400

Cys Arg Gln Leu Gly Cys Gly Trp Ala Thr Ser Ala Pro Gly Asn Ala
                405                 410                 415

Arg Phe Gly Gln Gly Ser Gly Pro Ile Val Leu Asp Asp Val Arg Cys
            420                 425                 430

Ser Gly Tyr Glu Ser Tyr Leu Trp Ser Cys Pro His Asn Gly Trp Leu
        435                 440                 445

Ser His Asn Cys Gln His Ser Glu Asp Ala Gly Val Ile Cys Ser Ala
    450                 455                 460

Ala His Ser Trp Ser Thr Pro Ser Pro Asp Thr Leu Pro Thr Ile Thr
465                 470                 475                 480

Leu Pro Ala Ser Thr Val Gly Ser Glu Ser Ser Leu Ala Leu Arg Leu
                485                 490                 495

Val Asn Gly Gly Asp Arg Cys Gln Gly Arg Val Glu Val Leu Tyr Arg
            500                 505                 510

Gly Ser Trp Gly Thr Val Cys Asp Asp Ser Trp Asp Thr Asn Asp Ala
        515                 520                 525

Asn Val Val Cys Arg Gln Leu Gly Cys Gly Trp Ala Met Leu Ala Pro
    530                 535                 540

Gly Asn Ala Arg Phe Gly Gln Gly Ser Gly Pro Ile Val Leu Asp Asp
545                 550                 555                 560

Val Arg Cys Ser Gly Asn Glu Ser Tyr Leu Trp Ser Cys Pro His Asn
                565                 570                 575

Gly Trp Leu Ser His Asn Cys Gly His Ser Glu Asp Ala Gly Val Ile
            580                 585                 590

Cys Ser Gly Pro Glu Ser Ser Leu Ala Leu Arg Leu Val Asn Gly Gly
        595                 600                 605

Asp Arg Cys Gln Gly Arg Val Glu Val Leu Tyr Arg Gly Ser Trp Gly
    610                 615                 620

Thr Val Cys Asp Asp Ser Trp Asp Thr Asn Asp Ala Asn Val Val Cys
625                 630                 635                 640

Arg Gln Leu Gly Cys Gly Trp Ala Met Ser Ala Pro Gly Asn Ala Arg
                645                 650                 655
```

Phe Gly Gln Gly Ser Gly Pro Ile Val Leu Asp Asp Val Arg Cys Ser
        660                 665                 670

Gly His Glu Ser Tyr Leu Trp Ser Cys Pro Asn Asn Gly Trp Leu Ser
        675                 680                 685

His Asn Cys Gly His His Glu Asp Ala Gly Val Ile Cys Ser Ala Ala
        690                 695                 700

Gln Ser Arg Ser Thr Pro Arg Pro Asp Thr Leu Ser Thr Ile Thr Leu
705                 710                 715                 720

Pro Pro Ser Thr Val Gly Ser Glu Ser Ser Leu Thr Leu Arg Leu Val
                725                 730                 735

Asn Gly Ser Asp Arg Cys Gln Gly Arg Val Glu Val Leu Tyr Arg Gly
                740                 745                 750

Ser Trp Gly Thr Val Cys Asp Asp Ser Trp Asp Thr Asn Asp Ala Asn
        755                 760                 765

Val Val Cys Arg Gln Leu Gly Cys Gly Trp Ala Met Ser Ala Pro Gly
        770                 775                 780

Asn Ala Arg Phe Gly Gln Gly Ser Gly Pro Ile Val Leu Asp Asp Val
785                 790                 795                 800

Arg Cys Ser Gly His Glu Ser Tyr Leu Trp Ser Cys Pro His Asn Gly
                805                 810                 815

Trp Leu Ser His Asn Cys Gly His His Glu Asp Ala Gly Val Ile Cys
                820                 825                 830

Ser Val Ser Gln Ser Arg Pro Thr Pro Ser Pro Asp Thr Trp Pro Thr
        835                 840                 845

Ser His Ala Ser Thr Ala Gly Ser Glu Ser Ser Leu Ala Leu Arg Leu
        850                 855                 860

Val Asn Gly Gly Asp Arg Cys Gln Gly Arg Val Glu Val Leu Tyr Arg
865                 870                 875                 880

Gly Ser Trp Gly Thr Val Cys Asp Asp Ser Trp Asp Thr Ser Asp Ala
                885                 890                 895

Asn Val Val Cys Arg Gln Leu Gly Cys Gly Trp Ala Thr Ser Ala Pro
                900                 905                 910

Gly Asn Ala Arg Phe Gly Gln Gly Ser Gly Pro Ile Val Leu Asp Asp
        915                 920                 925

Val Arg Cys Ser Gly Tyr Glu Ser Tyr Leu Trp Ser Cys Pro His Asn
        930                 935                 940

Gly Trp Leu Ser His Asn Cys Gln His Ser Glu Asp Ala Gly Val Ile
945                 950                 955                 960

Cys Ser Ala Ala His Ser Trp Ser Thr Ser Pro Ser Pro Asp Thr Leu Pro
                965                 970                 975

Thr Ile Thr Leu Pro Ala Ser Thr Val Gly Ser Glu Ser Ser Leu Ala
        980                 985                 990

Leu Arg Leu Val Asn Gly Gly Asp Arg Cys Gln Gly Arg Val Glu Val
        995                 1000                1005

Leu Tyr Gln Gly Ser Trp Gly Thr Val Cys Asp Asp Ser Trp Asp
        1010                1015                1020

Thr Asn Asp Ala Asn Val Val Cys Arg Gln Pro Gly Cys Gly Trp
        1025                1030                1035

Ala Met Ser Ala Pro Gly Asn Ala Arg Phe Gly Gln Gly Ser Gly
        1040                1045                1050

Pro Ile Val Leu Asp Asp Val Arg Cys Ser Gly His Glu Ser Tyr
        1055                1060                1065

```
Pro Trp Ser Cys Pro His Asn Gly Trp Leu Ser His Asn Cys Gly
    1070                1075                1080

His Ser Glu Asp Ala Gly Val Ile Cys Ser Ala Ser Gln Ser Arg
    1085                1090                1095

Pro Thr Pro Ser Pro Asp Thr Trp Pro Thr Ser His Ala Ser Thr
    1100                1105                1110

Ala Gly Ser Glu Ser Ser Leu Ala Leu Arg Leu Val Asn Gly Gly
    1115                1120                1125

Asp Arg Cys Gln Gly Arg Val Glu Val Leu Tyr Arg Gly Ser Trp
    1130                1135                1140

Gly Thr Val Cys Asp Asp Tyr Trp Asp Thr Asn Asp Ala Asn Val
    1145                1150                1155

Val Cys Arg Gln Leu Gly Cys Gly Trp Ala Met Ser Ala Pro Gly
    1160                1165                1170

Asn Ala Arg Phe Gly Gln Gly Ser Gly Pro Ile Val Leu Asp Asp
    1175                1180                1185

Val Arg Cys Ser Gly His Glu Ser Tyr Leu Trp Ser Cys Pro His
    1190                1195                1200

Asn Gly Trp Leu Ser His Asn Cys Gly His His Glu Asp Ala Gly
    1205                1210                1215

Val Ile Cys Ser Ala Ser Gln Ser Gln Pro Thr Pro Ser Pro Asp
    1220                1225                1230

Thr Trp Pro Thr Ser His Ala Ser Thr Ala Gly Ser Glu Ser Ser
    1235                1240                1245

Leu Ala Leu Arg Leu Val Asn Gly Gly Asp Arg Cys Gln Gly Arg
    1250                1255                1260

Val Glu Val Leu Tyr Arg Gly Ser Trp Gly Thr Val Cys Asp Asp
    1265                1270                1275

Tyr Trp Asp Thr Asn Asp Ala Asn Val Val Cys Arg Gln Leu Gly
    1280                1285                1290

Cys Gly Trp Ala Thr Ser Ala Pro Gly Asn Ala Arg Phe Gly Gln
    1295                1300                1305

Gly Ser Gly Pro Ile Val Leu Asp Asp Val Arg Cys Ser Gly His
    1310                1315                1320

Glu Ser Tyr Leu Trp Ser Cys Pro His Asn Gly Trp Leu Ser His
    1325                1330                1335

Asn Cys Gly His His Glu Asp Ala Gly Val Ile Cys Ser Ala Ser
    1340                1345                1350

Gln Ser Gln Pro Thr Pro Ser Pro Asp Thr Trp Pro Thr Ser His
    1355                1360                1365

Ala Ser Thr Ala Gly Ser Glu Ser Ser Leu Ala Leu Arg Leu Val
    1370                1375                1380

Asn Gly Gly Asp Arg Cys Gln Gly Arg Val Glu Val Leu Tyr Arg
    1385                1390                1395

Gly Ser Trp Gly Thr Val Cys Asp Asp Tyr Trp Asp Thr Asn Asp
    1400                1405                1410

Ala Asn Val Val Cys Arg Gln Leu Gly Cys Gly Trp Ala Thr Ser
    1415                1420                1425

Ala Pro Gly Asn Ala Arg Phe Gly Gln Gly Ser Gly Pro Ile Val
    1430                1435                1440

Leu Asp Asp Val Arg Cys Ser Gly His Glu Ser Tyr Leu Trp Ser
    1445                1450                1455
```

-continued

Cys Pro His Asn Gly Trp Leu Ser His Asn Cys Gly His His Glu
1460                1465                1470

Asp Ala Gly Val Ile Cys Ser Ala Ser Gln Ser Gln Pro Thr Pro
1475                1480                1485

Ser Pro Asp Thr Trp Pro Thr Ser Arg Ala Ser Thr Ala Gly Ser
1490                1495                1500

Glu Ser Thr Leu Ala Leu Arg Leu Val Asn Gly Gly Asp Arg Cys
1505                1510                1515

Arg Gly Arg Val Glu Val Leu Tyr Gln Gly Ser Trp Gly Thr Val
1520                1525                1530

Cys Asp Asp Tyr Trp Asp Thr Asn Asp Ala Asn Val Val Cys Arg
1535                1540                1545

Gln Leu Gly Cys Gly Trp Ala Met Ser Ala Pro Gly Asn Ala Gln
1550                1555                1560

Phe Gly Gln Gly Ser Gly Pro Ile Val Leu Asp Asp Val Arg Cys
1565                1570                1575

Ser Gly His Glu Ser Tyr Leu Trp Ser Cys Pro His Asn Gly Trp
1580                1585                1590

Leu Ser His Asn Cys Gly His His Glu Asp Ala Gly Val Ile Cys
1595                1600                1605

Ser Ala Ala Gln Ser Gln Ser Thr Pro Arg Pro Asp Thr Trp Leu
1610                1615                1620

Thr Thr Asn Leu Pro Ala Leu Thr Val Gly Ser Glu Ser Ser Leu
1625                1630                1635

Ala Leu Arg Leu Val Asn Gly Gly Asp Arg Cys Arg Gly Arg Val
1640                1645                1650

Glu Val Leu Tyr Arg Gly Ser Trp Gly Thr Val Cys Asp Asp Ser
1655                1660                1665

Trp Asp Thr Asn Asp Ala Asn Val Val Cys Arg Gln Leu Gly Cys
1670                1675                1680

Gly Trp Ala Met Ser Ala Pro Gly Asn Ala Arg Phe Gly Gln Gly
1685                1690                1695

Ser Gly Pro Ile Val Leu Asp Asp Val Arg Cys Ser Gly Asn Glu
1700                1705                1710

Ser Tyr Leu Trp Ser Cys Pro His Lys Gly Trp Leu Thr His Asn
1715                1720                1725

Cys Gly His His Glu Asp Ala Gly Val Ile Cys Ser Ala Thr Gln
1730                1735                1740

Ile Asn Ser Thr Thr Thr Asp Trp Trp His Pro Thr Thr Thr Thr
1745                1750                1755

Thr Ala Arg Pro Ser Ser Asn Cys Gly Gly Phe Leu Phe Tyr Ala
1760                1765                1770

Ser Gly Thr Phe Ser Ser Pro Ser Tyr Pro Ala Tyr Tyr Pro Asn
1775                1780                1785

Asn Ala Lys Cys Val Trp Glu Ile Glu Val Asn Ser Gly Tyr Arg
1790                1795                1800

Ile Asn Leu Gly Phe Ser Asn Leu Lys Leu Glu Ala His His Asn
1805                1810                1815

Cys Ser Phe Asp Tyr Val Glu Ile Phe Asp Gly Ser Leu Asn Ser
1820                1825                1830

Ser Leu Leu Leu Gly Lys Ile Cys Asn Asp Thr Arg Gln Ile Phe
1835                1840                1845

```
Thr Ser Ser Tyr Asn Arg Met Thr Ile His Phe Arg Ser Asp Ile
1850             1855                 1860

Ser Phe Gln Asn Thr Gly Phe Leu Ala Trp Tyr Asn Ser Phe Pro
1865             1870                 1875

Ser Asp Ala Thr Leu Arg Leu Val Asn Leu Asn Ser Ser Tyr Gly
1880             1885                 1890

Leu Cys Ala Gly Arg Val Glu Ile Tyr His Gly Gly Thr Trp Gly
1895             1900                 1905

Thr Val Cys Asp Asp Ser Trp Thr Ile Gln Glu Ala Glu Val Val
1910             1915                 1920

Cys Arg Gln Leu Gly Cys Gly Arg Ala Val Ser Ala Leu Gly Asn
1925             1930                 1935

Ala Tyr Phe Gly Ser Gly Ser Gly Pro Ile Thr Leu Asp Asp Val
1940             1945                 1950

Glu Cys Ser Gly Thr Glu Ser Thr Leu Trp Gln Cys Arg Asn Arg
1955             1960                 1965

Gly Trp Phe Ser His Asn Cys Asn His Arg Glu Asp Ala Gly Val
1970             1975                 1980

Ile Cys Ser Gly Asn His Leu Ser Thr Pro Ala Pro Phe Leu Asn
1985             1990                 1995

Ile Thr Arg Pro Asn Thr Asp Tyr Ser Cys Gly Gly Phe Leu Ser
2000             2005                 2010

Gln Pro Ser Gly Asp Phe Ser Ser Pro Phe Tyr Pro Gly Asn Tyr
2015             2020                 2025

Pro Asn Asn Ala Lys Cys Val Trp Asp Ile Glu Val Gln Asn Asn
2030             2035                 2040

Tyr Arg Val Thr Val Ile Phe Arg Asp Val Gln Leu Glu Gly Gly
2045             2050                 2055

Cys Asn Tyr Asp Tyr Ile Glu Val Phe Asp Gly Pro Tyr Arg Ser
2060             2065                 2070

Ser Pro Leu Ile Ala Arg Val Cys Asp Gly Ala Arg Gly Ser Phe
2075             2080                 2085

Thr Ser Ser Ser Asn Phe Met Ser Ile Arg Phe Ile Ser Asp His
2090             2095                 2100

Ser Ile Thr Arg Arg Gly Phe Arg Ala Glu Tyr Tyr Ser Ser Pro
2105             2110                 2115

Ser Asn Asp Ser Thr Asn Leu Leu Cys Leu Pro Asn His Met Gln
2120             2125                 2130

Ala Ser Val Ser Arg Ser Tyr Leu Gln Ser Leu Gly Phe Ser Ala
2135             2140                 2145

Ser Asp Leu Val Ile Ser Thr Trp Asn Gly Tyr Tyr Glu Cys Arg
2150             2155                 2160

Pro Gln Ile Thr Pro Asn Leu Val Ile Phe Thr Ile Pro Tyr Ser
2165             2170                 2175

Gly Cys Gly Thr Phe Lys Gln Ala Asp Asn Asp Thr Ile Asp Tyr
2180             2185                 2190

Ser Asn Phe Leu Thr Ala Ala Val Ser Gly Gly Ile Ile Lys Arg
2195             2200                 2205

Arg Thr Asp Leu Arg Ile His Val Ser Cys Arg Met Leu Gln Asn
2210             2215                 2220

Thr Trp Val Asp Thr Met Tyr Ile Ala Asn Asp Thr Ile His Val
2225             2230                 2235
```

Ala Asn Asn Thr Ile Gln Val Glu Val Gln Tyr Gly Asn Phe
    2240                2245                2250

Asp Val Asn Ile Ser Phe Tyr Thr Ser Ser Ser Phe Leu Tyr Pro
2255                2260                2265

Val Thr Ser Arg Pro Tyr Tyr Val Asp Leu Asn Gln Asp Leu Tyr
    2270                2275                2280

Val Gln Ala Glu Ile Leu His Ser Asp Ala Val Leu Thr Leu Phe
    2285                2290                2295

Val Asp Thr Cys Val Ala Ser Pro Tyr Ser Asn Asp Phe Thr Ser
    2300                2305                2310

Leu Thr Tyr Asp Leu Ile Arg Ser Gly Cys Val Arg Asp Asp Thr
    2315                2320                2325

Tyr Gly Pro Tyr Ser Ser Pro Ser Leu Arg Ile Ala Arg Phe Arg
    2330                2335                2340

Phe Arg Ala Phe His Phe Leu Asn Arg Phe Pro Ser Val Tyr Leu
    2345                2350                2355

Arg Cys Lys Met Val Val Cys Arg Ala Tyr Asp Pro Ser Ser Arg
    2360                2365                2370

Cys Tyr Arg Gly Cys Val Leu Arg Ser Lys Arg Asp Val Gly Ser
    2375                2380                2385

Tyr Gln Glu Lys Val Asp Val Leu Gly Pro Ile Gln Leu Gln
    2390                2395                2400

Thr Pro Pro Arg Arg Glu Glu Glu Pro Arg
    2405                2410

<210> SEQ ID NO 2
<211> LENGTH: 1092
<212> TYPE: PRT
<213> ORGANISM: Homo sapiens

<400> SEQUENCE: 2

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
                20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
                100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

```
Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
            195                 200                 205

Thr Cys Glu Glu Ala Arg Cys Lys Ser Leu Gly Arg Phe Pro Asn Gly
            210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
            245                 250                 255

Val Ile Ala Gly Gln Gly Val Ala Trp Thr Lys Met Pro Val Cys Glu
            260                 265                 270

Glu Ile Phe Cys Pro Ser Pro Pro Ile Leu Asn Gly Arg His Ile
            275                 280                 285

Gly Asn Ser Leu Ala Asn Val Ser Tyr Gly Ser Ile Val Thr Tyr Thr
            290                 295                 300

Cys Asp Pro Asp Pro Glu Glu Gly Val Asn Phe Ile Leu Ile Gly Glu
305                 310                 315                 320

Ser Thr Leu Arg Cys Thr Val Asp Ser Gln Lys Thr Gly Thr Trp Ser
            325                 330                 335

Gly Pro Ala Pro Arg Cys Glu Leu Ser Thr Ser Ala Val Gln Cys Pro
            340                 345                 350

His Pro Gln Ile Leu Arg Gly Arg Met Val Ser Gly Gln Lys Asp Arg
            355                 360                 365

Tyr Thr Tyr Asn Asp Thr Val Ile Phe Ala Cys Met Phe Gly Phe Thr
            370                 375                 380

Leu Lys Gly Ser Lys Gln Ile Arg Cys Asn Ala Gln Gly Thr Trp Glu
385                 390                 395                 400

Pro Ser Ala Pro Val Cys Glu Lys Glu Cys Gln Ala Pro Pro Asn Ile
            405                 410                 415

Leu Asn Gly Gln Lys Glu Asp Arg His Met Val Arg Phe Asp Pro Gly
            420                 425                 430

Thr Ser Ile Lys Tyr Ser Cys Asn Pro Gly Tyr Val Leu Val Gly Glu
            435                 440                 445

Glu Ser Ile Gln Cys Thr Ser Glu Gly Val Trp Thr Pro Pro Val Pro
            450                 455                 460

Gln Cys Lys Val Ala Ala Cys Glu Ala Thr Gly Arg Gln Leu Leu Thr
465                 470                 475                 480

Lys Pro Gln His Gln Phe Val Arg Pro Asp Val Asn Ser Ser Cys Gly
            485                 490                 495

Glu Gly Tyr Lys Leu Ser Gly Ser Val Tyr Gln Glu Cys Gln Gly Thr
            500                 505                 510

Ile Pro Trp Phe Met Glu Ile Arg Leu Cys Lys Glu Ile Thr Cys Pro
            515                 520                 525

Pro Pro Pro Val Ile Tyr Asn Gly Ala His Thr Gly Ser Ser Leu Glu
            530                 535                 540

Asp Phe Pro Tyr Gly Thr Thr Val Thr Tyr Thr Cys Asn Pro Gly Pro
545                 550                 555                 560

Glu Arg Gly Val Glu Phe Ser Leu Ile Gly Glu Ser Thr Ile Arg Cys
            565                 570                 575

Thr Ser Asn Asp Gln Glu Arg Gly Thr Trp Ser Gly Pro Ala Pro Leu
            580                 585                 590
```

```
Cys Lys Leu Ser Leu Leu Ala Val Gln Cys Ser His Val His Ile Ala
            595                 600                 605
Asn Gly Tyr Lys Ile Ser Gly Lys Glu Ala Pro Tyr Phe Tyr Asn Asp
        610                 615                 620
Thr Val Thr Phe Lys Cys Tyr Ser Gly Phe Thr Leu Lys Gly Ser Ser
625                 630                 635                 640
Gln Ile Arg Cys Lys Ala Asp Asn Thr Trp Asp Pro Glu Ile Pro Val
                645                 650                 655
Cys Glu Lys Gly Cys Gln Ser Pro Pro Gly Leu His His Gly Arg His
            660                 665                 670
Thr Gly Gly Asn Thr Val Phe Phe Val Ser Gly Met Thr Val Asp Tyr
        675                 680                 685
Thr Cys Asp Pro Gly Tyr Leu Leu Val Gly Asn Lys Ser Ile His Cys
690                 695                 700
Met Pro Ser Gly Asn Trp Ser Pro Ser Ala Pro Arg Cys Glu Glu Thr
705                 710                 715                 720
Cys Gln His Val Arg Gln Ser Leu Gln Glu Leu Pro Ala Gly Ser Arg
                725                 730                 735
Val Glu Leu Val Asn Thr Ser Cys Gln Asp Gly Tyr Gln Leu Thr Gly
            740                 745                 750
His Ala Tyr Gln Met Cys Gln Asp Ala Glu Asn Gly Ile Trp Phe Lys
        755                 760                 765
Lys Ile Pro Leu Cys Lys Val Ile His Cys His Pro Pro Pro Val Ile
770                 775                 780
Val Asn Gly Lys His Thr Gly Met Met Ala Glu Asn Phe Leu Tyr Gly
785                 790                 795                 800
Asn Glu Val Ser Tyr Glu Cys Asp Gln Gly Phe Tyr Leu Leu Gly Glu
                805                 810                 815
Lys Lys Leu Gln Cys Arg Ser Asp Ser Lys Gly His Gly Ser Trp Ser
            820                 825                 830
Gly Pro Ser Pro Gln Cys Leu Arg Ser Pro Pro Val Thr Arg Cys Pro
        835                 840                 845
Asn Pro Glu Val Lys His Gly Tyr Lys Leu Asn Lys Thr His Ser Ala
850                 855                 860
Tyr Ser His Asn Asp Ile Val Tyr Val Asp Cys Asn Pro Gly Phe Ile
865                 870                 875                 880
Met Asn Gly Ser Arg Val Ile Arg Cys His Thr Asp Asn Thr Trp Val
                885                 890                 895
Pro Gly Val Pro Thr Cys Ile Lys Lys Ala Phe Ile Gly Cys Pro Pro
            900                 905                 910
Pro Pro Lys Thr Pro Asn Gly Asn His Thr Gly Gly Asn Ile Ala Arg
        915                 920                 925
Phe Ser Pro Gly Met Ser Ile Leu Tyr Ser Cys Asp Gln Gly Tyr Leu
930                 935                 940
Leu Val Gly Glu Ala Leu Leu Leu Cys Thr His Glu Gly Thr Trp Ser
945                 950                 955                 960
Gln Pro Ala Pro His Cys Lys Glu Val Asn Cys Ser Ser Pro Ala Asp
                965                 970                 975
Met Asp Gly Ile Gln Lys Gly Leu Glu Pro Arg Lys Met Tyr Gln Tyr
            980                 985                 990
Gly Ala Val Val Thr Leu Glu Cys Glu Asp Gly Tyr Met Leu Glu Gly
        995                 1000                1005
```

```
Ser Pro Gln Ser Gln Cys Gln Ser Asp His Gln Trp Asn Pro Pro
    1010                1015                1020

Leu Ala Val Cys Arg Ser Arg Ser Leu Ala Pro Val Leu Cys Gly
    1025                1030                1035

Ile Ala Ala Gly Leu Ile Leu Leu Thr Phe Leu Ile Val Ile Thr
    1040                1045                1050

Leu Tyr Val Ile Ser Lys His Arg Ala Arg Asn Tyr Tyr Thr Asp
    1055                1060                1065

Thr Ser Gln Lys Glu Ala Phe His Leu Glu Ala Arg Glu Val Tyr
    1070                1075                1080

Ser Val Asp Pro Tyr Asn Pro Ala Ser
    1085                1090

<210> SEQ ID NO 3
<211> LENGTH: 225
<212> TYPE: PRT
<213> ORGANISM: Homo sapiens

<400> SEQUENCE: 3

Met Asp Gln Gln Ala Ile Tyr Ala Glu Leu Asn Leu Pro Thr Asp Ser
1                   5                   10                  15

Gly Pro Glu Ser Ser Pro Ser Ser Leu Pro Arg Asp Val Cys Gln
            20                  25                  30

Gly Ser Pro Trp His Gln Phe Ala Leu Lys Leu Ser Cys Ala Gly Ile
            35                  40                  45

Ile Leu Leu Val Leu Val Val Thr Gly Leu Ser Val Ser Val Thr Ser
    50                  55                  60

Leu Ile Gln Lys Ser Ser Ile Glu Lys Cys Ser Val Asp Ile Gln Gln
65                  70                  75                  80

Ser Arg Asn Lys Thr Thr Glu Arg Pro Gly Leu Leu Asn Cys Pro Ile
                85                  90                  95

Tyr Trp Gln Gln Leu Arg Glu Lys Cys Leu Leu Phe Ser His Thr Val
            100                 105                 110

Asn Pro Trp Asn Asn Ser Leu Ala Asp Cys Ser Thr Lys Glu Ser Ser
            115                 120                 125

Leu Leu Leu Ile Arg Asp Lys Asp Glu Leu Ile His Thr Gln Asn Leu
    130                 135                 140

Ile Arg Asp Lys Ala Ile Leu Phe Trp Ile Gly Leu Asn Phe Ser Leu
145                 150                 155                 160

Ser Glu Lys Asn Trp Lys Trp Ile Asn Gly Ser Phe Leu Asn Ser Asn
                165                 170                 175

Asp Leu Glu Ile Arg Gly Asp Ala Lys Glu Asn Ser Cys Ile Ser Ile
            180                 185                 190

Ser Gln Thr Ser Val Tyr Ser Glu Tyr Cys Ser Thr Glu Ile Arg Trp
            195                 200                 205

Ile Cys Gln Lys Glu Leu Thr Pro Val Arg Asn Lys Val Tyr Pro Asp
    210                 215                 220

Ser
225

<210> SEQ ID NO 4
<211> LENGTH: 326
<212> TYPE: PRT
<213> ORGANISM: Homo sapiens
```

<400> SEQUENCE: 4

```
Met Glu Leu Ser Gly Ala Thr Met Ala Arg Gly Leu Ala Val Leu Leu
1               5                  10                  15

Val Leu Phe Leu His Ile Lys Asn Leu Pro Ala Gln Ala Ala Asp Thr
            20                  25                  30

Cys Pro Glu Val Lys Val Gly Leu Glu Gly Ser Asp Lys Leu Thr
        35                  40                  45

Ile Leu Arg Gly Cys Pro Leu Pro Gly Ala Pro Gly Pro Lys Gly
    50                  55                  60

Glu Ala Gly Val Ile Gly Glu Arg Gly Glu Arg Gly Leu Pro Gly Ala
65                  70                  75                  80

Pro Gly Lys Ala Gly Pro Val Gly Pro Lys Gly Asp Arg Gly Glu Lys
            85                  90                  95

Gly Met Arg Gly Glu Lys Gly Asp Ala Gly Gln Ser Gln Ser Cys Ala
                100                 105                 110

Thr Gly Pro Arg Asn Cys Lys Asp Leu Leu Asp Arg Gly Tyr Phe Leu
            115                 120                 125

Ser Gly Trp His Thr Ile Tyr Leu Pro Asp Cys Arg Pro Leu Thr Val
130                 135                 140

Leu Cys Asp Met Asp Thr Asp Gly Gly Gly Trp Thr Val Phe Gln Arg
145                 150                 155                 160

Arg Met Asp Gly Ser Val Asp Phe Tyr Arg Asp Trp Ala Ala Tyr Lys
                165                 170                 175

Gln Gly Phe Gly Ser Gln Leu Gly Glu Phe Trp Leu Gly Asn Asp Asn
            180                 185                 190

Ile His Ala Leu Thr Ala Gln Gly Ser Ser Glu Leu Arg Val Asp Leu
        195                 200                 205

Val Asp Phe Glu Gly Asn His Gln Phe Ala Lys Tyr Lys Ser Phe Lys
    210                 215                 220

Val Ala Asp Glu Ala Glu Lys Tyr Lys Leu Val Leu Gly Ala Phe Val
225                 230                 235                 240

Gly Gly Ser Ala Gly Asn Ser Leu Thr Gly His Asn Asn Phe Phe
                245                 250                 255

Ser Thr Lys Asp Gln Asp Asn Asp Val Ser Ser Asn Cys Ala Glu
            260                 265                 270

Lys Phe Gln Gly Ala Trp Trp Tyr Ala Asp Cys His Ala Ser Asn Leu
275                 280                 285

Asn Gly Leu Tyr Leu Met Gly Pro His Glu Ser Tyr Ala Asn Gly Ile
    290                 295                 300

Asn Trp Ser Ala Ala Lys Gly Tyr Lys Tyr Ser Tyr Lys Val Ser Glu
305                 310                 315                 320

Met Lys Val Arg Pro Ala
                325
```

```
<210> SEQ ID NO 5
<211> LENGTH: 742
<212> TYPE: PRT
<213> ORGANISM: Homo sapiens
```

<400> SEQUENCE: 5

```
Met Lys Asp Asp Phe Ala Glu Glu Glu Val Gln Ser Phe Gly Tyr
1               5                  10                  15

Lys Arg Phe Gly Ile Gln Glu Gly Thr Gln Cys Thr Lys Cys Lys Asn
            20                  25                  30
```

```
Asn Trp Ala Leu Lys Phe Ser Ile Ile Leu Leu Tyr Ile Leu Cys Ala
         35                  40                  45

Leu Leu Thr Ile Thr Val Ala Ile Leu Gly Tyr Lys Val Val Glu Lys
 50                  55                  60

Met Asp Asn Val Thr Gly Gly Met Glu Thr Ser Arg Gln Thr Tyr Asp
 65                  70                  75                  80

Asp Lys Leu Thr Ala Val Glu Ser Asp Leu Lys Lys Leu Gly Asp Gln
                 85                  90                  95

Thr Gly Lys Lys Ala Ile Ser Thr Asn Ser Glu Leu Ser Thr Phe Arg
                100                 105                 110

Ser Asp Ile Leu Asp Leu Arg Gln Gln Leu Arg Glu Ile Thr Glu Lys
             115                 120                 125

Thr Ser Lys Asn Lys Asp Thr Leu Glu Lys Leu Gln Ala Ser Gly Asp
130                 135                 140

Ala Leu Val Asp Arg Gln Ser Gln Leu Lys Glu Thr Leu Glu Asn Asn
145                 150                 155                 160

Ser Phe Leu Ile Thr Thr Val Asn Lys Thr Leu Gln Ala Tyr Asn Gly
                165                 170                 175

Tyr Val Thr Asn Leu Gln Gln Asp Thr Ser Val Leu Gln Gly Asn Leu
             180                 185                 190

Gln Asn Gln Met Tyr Ser His Asn Val Val Ile Met Asn Leu Asn Asn
         195                 200                 205

Leu Asn Leu Thr Gln Val Gln Gln Arg Asn Leu Ile Thr Asn Leu Gln
 210                 215                 220

Arg Ser Val Asp Asp Thr Ser Gln Ala Ile Gln Arg Ile Lys Asn Asp
225                 230                 235                 240

Phe Gln Asn Leu Gln Gln Val Phe Leu Gln Ala Lys Lys Asp Thr Asp
                245                 250                 255

Trp Leu Lys Glu Lys Val Gln Ser Leu Gln Thr Leu Ala Ala Asn Asn
                260                 265                 270

Ser Ala Leu Ala Lys Ala Asn Asn Asp Thr Leu Glu Asp Met Asn Ser
        275                 280                 285

Gln Leu Asn Ser Phe Thr Gly Gln Met Glu Asn Ile Thr Thr Ile Ser
 290                 295                 300

Gln Ala Asn Glu Gln Asn Leu Lys Asp Leu Gln Asp Leu His Lys Asp
305                 310                 315                 320

Ala Glu Asn Arg Thr Ala Ile Lys Phe Asn Gln Leu Glu Arg Phe
                325                 330                 335

Gln Leu Phe Glu Thr Asp Ile Val Asn Ile Ile Ser Asn Ile Ser Tyr
                340                 345                 350

Thr Ala His His Leu Arg Thr Leu Thr Ser Asn Leu Asn Glu Val Arg
             355                 360                 365

Thr Thr Cys Thr Asp Thr Leu Thr Lys His Thr Asp Asp Leu Thr Ser
 370                 375                 380

Leu Asn Asn Thr Leu Ala Asn Ile Arg Leu Asp Ser Val Ser Leu Arg
385                 390                 395                 400

Met Gln Gln Asp Leu Met Arg Ser Arg Leu Asp Thr Glu Val Ala Asn
                405                 410                 415

Leu Ser Val Ile Met Glu Glu Met Lys Leu Val Asp Ser Lys His Gly
                420                 425                 430

Gln Leu Ile Lys Asn Phe Thr Ile Leu Gln Gly Pro Pro Gly Pro Arg
             435                 440                 445
```

-continued

```
Gly Pro Arg Gly Asp Arg Gly Ser Gln Gly Pro Pro Gly Pro Thr Gly
    450                 455                 460

Asn Lys Gly Gln Lys Gly Glu Lys Gly Glu Pro Gly Pro Pro Gly Pro
465                 470                 475                 480

Ala Gly Glu Arg Gly Pro Ile Gly Pro Ala Gly Pro Pro Gly Glu Arg
                485                 490                 495

Gly Gly Lys Gly Ser Lys Gly Ser Gln Gly Pro Lys Gly Ser Arg Gly
            500                 505                 510

Ser Pro Gly Lys Pro Gly Pro Gln Gly Ser Ser Gly Asp Pro Gly Pro
            515                 520                 525

Pro Gly Pro Pro Gly Lys Glu Gly Leu Pro Gly Pro Gln Gly Pro Pro
530                 535                 540

Gly Phe Gln Gly Leu Gln Gly Thr Val Gly Glu Pro Gly Val Pro Gly
545                 550                 555                 560

Pro Arg Gly Leu Pro Gly Leu Pro Gly Val Pro Gly Met Pro Gly Pro
                565                 570                 575

Lys Gly Pro Pro Gly Pro Pro Gly Pro Ser Gly Ala Val Val Pro Leu
            580                 585                 590

Ala Leu Gln Asn Glu Pro Thr Pro Ala Pro Glu Asp Asn Gly Cys Pro
            595                 600                 605

Pro His Trp Lys Asn Phe Thr Asp Lys Cys Tyr Tyr Phe Ser Val Glu
    610                 615                 620

Lys Glu Ile Phe Glu Asp Ala Lys Leu Phe Cys Glu Asp Lys Ser Ser
625                 630                 635                 640

His Leu Val Phe Ile Asn Thr Arg Glu Glu Gln Gln Trp Ile Lys Lys
                645                 650                 655

Gln Met Val Gly Arg Glu Ser His Trp Ile Gly Leu Thr Asp Ser Glu
            660                 665                 670

Arg Glu Asn Glu Trp Lys Trp Leu Asp Gly Thr Ser Pro Asp Tyr Lys
            675                 680                 685

Asn Trp Lys Ala Gly Gln Pro Asp Asn Trp Gly His Gly His Gly Pro
        690                 695                 700

Gly Glu Asp Cys Ala Gly Leu Ile Tyr Ala Gly Gln Trp Asn Asp Phe
705                 710                 715                 720

Gln Cys Glu Asp Val Asn Asn Phe Ile Cys Glu Lys Asp Arg Glu Thr
                725                 730                 735

Val Leu Ser Ser Ala Leu
            740

<210> SEQ ID NO 6
<211> LENGTH: 500
<212> TYPE: PRT
<213> ORGANISM: Homo sapiens

<400> SEQUENCE: 6

Met Lys Phe Leu Ala Val Leu Leu Ala Ala Gly Met Leu Ala Phe Leu
1               5                   10                  15

Gly Ala Val Ile Cys Ile Ile Ala Ser Val Pro Leu Ala Ala Ser Pro
                20                  25                  30

Ala Arg Ala Leu Pro Gly Gly Ala Asp Asn Ala Ser Val Ala Ser Gly
            35                  40                  45

Ala Ala Ala Ser Pro Gly Pro Gln Arg Ser Leu Ser Ala Leu His Gly
        50                  55                  60

Ala Gly Gly Ser Ala Gly Pro Pro Ala Leu Pro Gly Ala Pro Ala Ala
65                  70                  75                  80
```

```
Ser Ala His Pro Leu Pro Pro Gly Pro Leu Phe Ser Arg Phe Leu Cys
                85                  90                  95

Thr Pro Leu Ala Ala Ala Cys Pro Ser Gly Ala Gln Gln Gly Asp Ala
            100                 105                 110

Ala Gly Ala Ala Pro Gly Glu Arg Glu Leu Leu Leu Leu Leu Gln Ser
        115                 120                 125

Thr Ala Glu Gln Leu Arg Gln Thr Ala Leu Gln Gln Glu Ala Arg Ile
    130                 135                 140

Arg Ala Asp Gln Asp Thr Ile Arg Glu Leu Thr Gly Lys Leu Gly Arg
145                 150                 155                 160

Cys Glu Ser Gly Leu Pro Arg Gly Leu Gln Gly Ala Gly Pro Arg Arg
                165                 170                 175

Asp Thr Met Ala Asp Gly Pro Trp Asp Ser Pro Ala Leu Ile Leu Glu
            180                 185                 190

Leu Glu Asp Ala Val Arg Ala Leu Arg Asp Arg Ile Asp Arg Leu Glu
        195                 200                 205

Gln Glu Leu Pro Ala Arg Val Asn Leu Ser Ala Ala Pro Ala Pro Val
    210                 215                 220

Ser Ala Val Pro Thr Gly Leu His Ser Lys Met Asp Gln Leu Glu Gly
225                 230                 235                 240

Gln Leu Leu Ala Gln Val Leu Ala Leu Glu Lys Glu Arg Val Ala Leu
                245                 250                 255

Ser His Ser Ser Arg Arg Gln Arg Gln Glu Val Glu Lys Glu Leu Asp
            260                 265                 270

Val Leu Gln Gly Arg Val Ala Glu Leu Glu His Gly Ser Ser Ala Tyr
        275                 280                 285

Ser Pro Pro Asp Ala Phe Lys Ile Ser Ile Pro Ile Arg Asn Asn Tyr
    290                 295                 300

Met Tyr Ala Arg Val Arg Lys Ala Leu Pro Glu Leu Tyr Ala Phe Thr
305                 310                 315                 320

Ala Cys Met Trp Leu Arg Ser Arg Ser Ser Gly Thr Gly Gln Gly Thr
                325                 330                 335

Pro Phe Ser Tyr Ser Val Pro Gly Gln Ala Asn Glu Ile Val Leu Leu
            340                 345                 350

Glu Ala Gly His Glu Pro Met Glu Leu Leu Ile Asn Asp Lys Val Ala
        355                 360                 365

Gln Leu Pro Leu Ser Leu Lys Asp Asn Gly Trp His His Ile Cys Ile
    370                 375                 380

Ala Trp Thr Thr Arg Asp Gly Leu Trp Ser Ala Tyr Gln Asp Gly Glu
385                 390                 395                 400

Leu Gln Gly Ser Gly Glu Asn Leu Ala Ala Trp His Pro Ile Lys Pro
                405                 410                 415

His Gly Ile Leu Ile Leu Gly Gln Glu Gln Asp Thr Leu Gly Gly Arg
            420                 425                 430

Phe Asp Ala Thr Gln Ala Phe Val Gly Asp Ile Ala Gln Phe Asn Leu
        435                 440                 445

Trp Asp His Ala Leu Thr Pro Ala Gln Val Leu Gly Ile Ala Asn Cys
    450                 455                 460

Thr Ala Pro Leu Leu Gly Asn Val Leu Pro Trp Glu Asp Lys Leu Val
465                 470                 475                 480
```

```
Glu Ala Phe Gly Gly Ala Thr Lys Ala Ala Phe Asp Val Cys Lys Gly
            485                 490                 495
Arg Ala Lys Ala
        500
```

IMMUNOLOGICAL EXTRACT AND METHOD OF PRODUCTION

CROSS-REFERENCE TO RELATED APPLICATIONS

This application is a U.S. National Phase application under 35 U.S.C. § 371 of International Patent Application No. PCT/SG2019/050200, filed on Apr. 10, 2019, which claims priority to Singapore Patent Application No. SG 10201802979V, filed on Apr. 10, 2018, all of which applications are incorporated herein by reference in their entireties.

Sequence Listing

The instant application contains a Sequence Listing which has been submitted electronically in ASCII format and is hereby incorporated by reference in its entirety. Said ASCII copy, created on Apr. 9, 2019, is named 254111_000003_SL.txt and is 46,371 bytes in size.

TECHNICAL FIELD OF INVENTION

The present invention relates to methods of preparing an immunological extract from mixtures comprising bird's nest raw materials, and optionally other materials, and the extracts obtainable from the methods.

BACKGROUND OF INVENTION

Edible bird's nest (EBN) is the nest made from the saliva of swiftlets naturally found in the South-east Asian region. The abandoned nests are harvested from the wild or from specially built housing for swiftlets. It has been reported that EBN exhibited various bioactivities and nutritional value that include potential for mitogenic response, epidermal growth factor (EGF)-like activity, anti-influenza virus, haemagglutination-inhibitory activity, lectin-binding activity, improvement of bone strength and dermal thickness, and hormone content. Processing of EBN can be different depending on the application. Ongoing investigations have been carried out to elucidate the biological and medical functions of the edible bird's nest.

Currently, EBN is used in the form of a soup or other drinks by boiling the EBN in water and consuming. The molecules of EBN in such a scenario are large biomacromolecules that are difficult for the body to digest and absorb. As a result, the bioavailability of the beneficial components of EBN prepared in such a manner is low, and the beneficial effects of EBN is not maximised.

However, consuming whole EBN may lead to immunoglobulin E (IgE) mediated anaphylaxis (Goh et al., 2001, J. Allergy Clin. Immun., 107(6), 1082-1088) and EBN is thought to be the most common cause of food-induced anaphylaxis which could be life-threatening among children.

Another problem with crude EBN is the presence of undesirable compounds either due to natural causes or added intentionally during processing. Adulteration of EBN commonly takes place decreasing the quality of the EBN. Adulterants used include pig skin, agar, red seaweed and karaya gum. In order to camouflage adulterants and waste matters, bleaches are often added.

Of particular concern is the presence of nitrite salts which is derived mainly from the faeces of the swiftlets. Nitrites can also be added to white bird's nest during processing to turn it into red bird's nest which is commercially more valuable. Ingestion of excessive nitrites had been linked to cancer (Bryan et al. Food Chem. Toxicol. 2012, 50 (10), 3646-3654).

Viruses, bacteria and fungi could contaminate EBN in the wild or in the factory during processing. Concerns with regards to avian flu in wild birds can lead to restriction of imports of whole EBN itself.

Therefore, there is a need to improve the processing of EBN to improve the overall quality and beneficial properties to the consumer. By extracting and isolating desirable compounds from EBN, harmful effects are avoided or minimised while maximising the therapeutic benefits of EBN.

Further, bioactive molecules like opsonins, complement proteins, lectins, ficolins, collectins, and pentraxins are extracted mainly from animal parts or genetically modified microorganisms cloned in bioreactors. There is a lack of a standard for consistency in purity and yields and safety aspects of the extracted products. The process described herein solves the issues of safety and sustainability as edible bird's nest (EBN), or EBN mixtures containing hasma or coral seaweed, are very rich and abundant sources for such bioactive factors.

The listing or discussion of an apparently prior-published document in this specification should not necessarily be taken as an acknowledgement that the document is part of the state of the art or is common general knowledge.

Any document referred to herein is hereby incorporated by reference in its entirety.

SUMMARY OF INVENTION

In a first aspect of the invention, there is provided a method of preparing an extract from edible bird's nest, the method comprising: preparing an edible bird's nest (EBN) mixture; and contacting the mixture with an extraction solution to bind a molecule in the mixture, wherein the extraction solution comprises at least one binding moiety selected from the group comprising an opsonin binding moiety, a complement protein binding moiety, a lectin binding moiety, a ficolin binding moiety, a collectin binding moiety, and a pentraxin binding moiety.

The term "contacting" refers to the components of the EBN mixture and extraction solution interacting with each other, preferably the interaction should lead to the formation of a bond, which is reversible, between the binding moiety and the target molecule.

The term "binding moiety" refers to any molecule and/or functional group that selectively targets and binds to the molecule of interest. For example, an opsonin binding moiety is any molecule that binds to an opsonin molecule. Examples of suitable binding moiety may include antibodies, antibody fragments, antibody mimetics, cells with receptors, and molecules that mimic the binding function of the receptor. For example, a "lectin binding moiety" could be a cell expressing a lectin binding receptor on the cell surface, and so forth. In another example, a "lectin binding moiety" includes an antibody which binds lectin, or the lectin (antigen) binding site of an antibody, antibody fragment, or antibody mimetic, and so forth. The binding moiety should preferably bind to the molecule with a $K_D$ in the micromolar or lower region. For example, the binding moiety could bind to the molecule with a $K_D$ of less than $10^{-4}$, $10^{-5}$, $10^{-6}$, $10^{-7}$, $10^{-8}$, $10^{-8}$, $10^{-10}$, $10^{-11}$, $10^{-12}$, or less. The lower the $K_D$ value the stronger the binding affinity. The binding moiety of the extraction solution is preferably capable of binding to its target with an affinity that is at least two-fold, 10-fold, 50-fold, 100-fold or greater than its affinity for binding to another non-target molecule.

The binding moiety to be used may be naturally occurring, semi-synthetic or synthetic, for example tagged binding moiety that can facilitate the separation of the binding moiety from the EBN mixture may be used. Additionally, the binding moiety used to extract the target molecule could be bound to a solid support. The solid support could be made of a ferromagnetic material or conventional inert support material. The binding moiety may be commercially available and can be used as such. If modifications of the binding moiety are desired, there are many methods as commonly known in the literature to modify to obtain the desired characteristics.

FIG. 9 shows how cells with the desired receptor may be produced. In FIG. 9 panel (a), all mRNA is extracted from cells that normally express the receptor of interest and reverse-transcribed into double-stranded cDNA. The entire population of cDNAs is inserted into plasmid expression vectors in between a strong promoter and a terminator of transcription. The plasmids are transfected into bacterial cells that do not normally express the receptor of interest. The resulting cDNA library is divided into pools, each containing about 1000 different cDNAs. Panel (b) of FIG. 9 further shows that the plasmids in each pool are transfected into a population of cultured cells (e.g., COS cells) that lack the receptor of interest. Only transfected cells that contain the cDNA encoding the desired receptor synthesise it; other transfected cells produce irrelevant proteins. To detect the few cells producing the desired receptor, a radiolabeled ligand specific for the receptor is added to the culture dishes containing the transfected cells; the cells are fixed and subjected to autoradiography. Positive cells synthesizing the specific receptor will be covered with many grains. Alternatively, transfected cells can be treated with a fluorescent-labeled ligand and passed through a fluorescence-activated cell sorter. Cells expressing the receptor will bind the fluorescent label and be separated from those that do not. Plasmid cDNA pools giving rise to a positive signal are maintained in bacteria and subdivided into smaller pools, each of which is rescreened by transfection into cultured cells. After several cycles of screening and subdividing positive cDNA pools, a pure cDNA clone encoding the desired receptor is obtained. Detailed methods may be found in A. Aruffo and B. Seed, *Molecular Cloning of a CD28 cDNA by a high-efficiency COS cell expression system*, Proc. Nat'l. Acad. Sci. USA, 1987, 84, 8573; and A. D'Andrea, H. F. Lodish, and G. Wong, *Expression Cloning of the murine erythropoietin receptor*, Cell, 1989, Vol. 57, 277, which are both incorporated herein by reference. The pure cDNA clone may then be used to produce cells with the desired receptor of interest.

The cDNA refers to complementary DNA and refers to nucleic acid molecules having a nucleotide sequence complementary to a desired coding polynucleotide, for example RNA, in particular mRNA. The term "complementary" refer to sequences of polynucleotides which is capable of forming Watson and Crick base pairing with nother specified throughout the entirety of the complementary region. Complementary bases are generally, A and T (A and U), or C and G. The desired coding polynucleotide includes sequences having at least 50%, 60%, 70%, 80%, 90%, 95%, or 99% identity to a polynucleotide sequence which encodes the desired polypeptide.

In an example, the binding moiety may be a protein produced by the expression of the cDNA in an expression system. Common examples of expression systems include cell-based systems and cell-free systems. Cell-based systems include those derived from bacteria, yeast, insect cells, mammalian cells and filamentous fungi. Non-limiting examples of bacteria expression systems include *Escherichia coli* (*E. coli*), and *Pseudomonas fluorescens* (*P. fluorescens*). Non-limiting examples of eukaryotic systems include yeasts like *Saccharomyces cerevisiae* (*S. cerevisiae*) and *Pichia pastoris*, filamentous fungi like *Aspergillus, Trichoderma*, and Myceliphthora thermophile, insect cells infected with and without baculovirus like Sf9 and Sf21 from *Spodoptera frugiperda* cells, and mammalian cells like Chinese Hamster ovary (CHO) and Human embryonic kidney (HEK) cells. Cell-free production of proteins may also be performed in-vitro using purified RNA polymerase, ribosomes, tRNA and ribonucletides which may be obtained synthetically, from cells and/or from a cell-based expression system. The different expression systems each have its own advantages and the choice of the expression system depends in part on the nature of the protein and the intended use. For example, if post-translation modification of the protein is required a eukaryotic system is generally a better choice. It may also be possible for multiple cells to be used in the expression system to produce the protein. Often the expression systems includes an affinity tag attached to the protein to facilitate the purification of the expressed protein. These affinity tags bind specifically with specific partner ligands, for example immobilised on a solid support, enabling separation of the affinity tag and protein construct. The expressed protein may be isolated with the affinity tag or by cleavage of the affinity tag to release the desired protein. Non-limiting examples includes a His tag and a Strep-tag. The His-tag binds strongly to divalent metal ions like nickel and cobalt, while the Strep-tag binds specifically to an engineered streptavidin. Other purification methods may also be utilised as required.

If antibodies are used, the antibodies may exist in a variety of forms including, for example, polyclonal antibodies, monoclonal antibodies, humanised antibodies and human antibodies. Examples of antibody fragments may include Fab, Fab', F(ab')2, Fv, linear antibodies, single chain (scFv) antibodies, single-domain antibodies (sdAb). Methods of producing these binding moieties may be made by any suitable method. One method of obtaining antibodies is to immunise suitable host animals with an immunogen and to follow standard procedures for polyclonal or monoclonal antibody production. The immunogen will facilitate presentation of the immunogen on the cell surface. Immunisation of a suitable host can be carried out in a number of ways. Nucleic acid sequences encoding a polypeptide or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding the polypeptide, or immunogenic surfaces thereof, can be expressed in cells in vitro, followed by isolation of the polypeptide and administration of the polypeptide to a suitable host in which antibodies are raised. Alternatively, antibodies against the polypeptide may be derived from an antibody phage display library. A bacteriophage is capable of infecting and reproducing within bacteria, which can be engineered, when combined with human antibody genes, to display human antibody proteins. Phage display is the process by which the phase is made to "display" the human antibody proteins on its surface. Genes from the human antibody gene libraries are inserted into a population of phage. Each phage carries the genes for a different antibody and thus displays a different antibody on its surface.

Antibodies made by any method known in the art may be further purified from the host. Antibody purification methods may include salt precipitation, ion exchange chromatography, gel filtration chromatography, and affinity chromatography, for example with protein A, protein G, hydroxyapatite and anti-immunoglobulin.

Antibodies may be conveniently produced from hybridoma cells engineered to express the antibody. Methods of making hybridomas are well known in the art. The hybridoma cells can be cultured in a suitable medium and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naïve histocompatible or immunotolerant mammal, especially a mouse. The mammal may be primed for ascites production by prior administration of a suitable composition (e.g. Pristane).

The term "antibody mimetic" or "antibody mimic" means a molecule which specifically binds an antigen, but is not structurally related to antibodies. Typically, antibody mimetics specifically binding to a target are produced by screening libraries of mutagenized molecular scaffolds. Examples of molecular scaffolds include, without limitation, a fibronectin III (FN3) domain. The molecular scaffold is typically a smaller molecule than an antibody (e.g. about 50-200 residues). Examples of antibody mimetics include, without limitation, affibodies, affilins, affitins, anticalins, avimers, DARPins, Kunitz domain derived peptides, knottins, and monobodies. A monobody comprise a fibronectin type III domain (FN3) as a molecular scaffold. Monobodies are produced from combinatorial libraries in which portions of the FN3 scaffold are diversified using highly tailored mixtures of amino acids by utilising phage display and yeast surface display techniques.

The term "lectin" in the context of the invention is a carbohydrate-binding protein and excludes ficolins and collectins. The term "opsonin" refers to any compound or molecules that enhances phagocytosis excluding complement proteins, lectins, ficolins, collectins, and pentraxins.

Preferably, the mixture further comprises seaweed and/or hasma. Hasma (hashima) is made from the dried fatty tissue near the fallopian tubes of true frogs. Seaweed or macroalgae refers to several species of macroscopic, multicellular, marine algae, and only includes those which are edible. Common edible seaweed that may be used include red algae, brown algae and green algae.

Preferably, the opsonin binding moiety has a molecular weight of about 10 kDa to about 750 kDa. In an example, the opsonin binding moiety comprises SEQ ID No. 1.

Preferably, the complement protein binding moiety has a molecular weight of about 20 kDa to about 7000 kDa. Examples of the complement protein binding moiety include a molecular weight of about 50 kDa to about 7000 kDa, and a molecular weight of about 20 kDa to about 1000 kDa. In an example, the complement protein binding moiety comprises SEQ ID No. 2.

Preferably, the lectin binding moiety has a molecular weight of about 20 kDa to about 1000 kDa. In an example, the lectin binding moiety comprises SEQ ID No. 3.

Preferably, the ficolin binding moiety has a molecular weight of about 15 kDa to about 900 kDa. In an example, the ficolin binding moiety comprises SEQ ID No. 4.

Preferably, the collectin binding moiety has a molecular weight of about 15 kDa to about 900 kDa. In an example, the collectin binding moiety comprises SEQ ID No. 5.

Preferably, the pentraxin binding moiety has a molecular weight of about 20 kDa to about 1000 kDa. In an example, the pentraxin binding moiety comprises SEQ ID No. 6.

Preferably, the binding moiety is a receptor protein. In an example, the receptor protein is anchored to a cell or may be isolated in purified form. The molecular weights of the binding moieties above refer to the receptor protein molecular weight.

Preferably, the at least one binding moiety comprises any one selected from:
i) the lectin binding moiety and the opsonin binding moiety;
ii) the lectin binding moiety, the complement protein binding moiety, the opsonin binding moiety, the ficolin binding moiety, the collectin binding moiety, and the pentraxin binding moiety;
iii) the lectin binding moiety, the complement protein binding moiety, and the opsonin binding moiety;
iv) the opsonin binding moiety, and the pentraxin binding moiety;
v) the ficolin binding moiety, the collectin binding moiety, and the pentraxin binding moiety;
vi) the complement protein binding moiety, the ficolin binding moiety, and the collectin binding moiety; and
vii) the lectin binding moiety, the opsonin binding moiety, and the collectin binding moiety.

More preferably, the at least one binding moiety comprises any one selected from:
i) 50% to 90% of the lectin binding moiety and 10% to 50% of the opsonin binding moiety;
ii) 10% to 30% of the lectin binding moiety, 10% to 30% of the complement protein binding moiety, 10% to 30% of the opsonin binding moiety, 5% to 15% of the ficolin binding moiety, 5% to 15% of the collectin binding moiety, and 10% to 30% of the pentraxin binding moiety;
iii) 5% to 45% of the lectin binding moiety, 35% to 65% of the complement protein binding moiety, and 5% to 45% of the opsonin binding moiety;
iv) 10% to 90% of the opsonin binding moiety, and 10% to 90% of the pentraxin binding moiety;
v) 30% to 50% of the ficolin binding moiety, 10% to 50% of the collectin binding moiety, and 10% to 50% of the pentraxin binding moiety;
vi) 55% to 85% of the complement protein binding moiety, 5% to 15% of the ficolin binding moiety, and 10% to 30% of the collectin binding moiety; and
vii) 5% to 15% of the lectin binding moiety, 10% to 30% of the opsonin binding moiety, and 55% to 85% of the collectin binding moiety. The percentage provided for each binding moiety is the percentage weight of each binding moiety relative to the total weight of the binding moieties present. Therefore, the binding moiety may be dissolved in a solvent like water, or buffer, but the percentage is for the binding moiety/moieties present.

Preferably, the at least one binding moiety comprises any one selected from:
i) 70% lectin of the binding moiety and 30% opsonin of the binding moiety;

ii) 20% lectin of the binding moiety, 20% complement protein of the binding moiety, 20% opsonin of the binding moiety, 20% pentraxin of the binding moiety, 10% ficolin of the binding moiety, and 10% collectin of the binding moiety;
iii) 50% complement protein of the binding moiety, 25% lectin of the binding moiety and 25% opsonin of the binding moiety;
iv) 50% opsonin of the binding moiety and 50% pentraxin of the binding moiety;
v) 40% ficolin of the binding moiety, 30% collectin of the binding moiety and 30% pentraxin of the binding moiety;
vi) 10% ficolin of the binding moiety, 20% collectin of the binding moiety and 70% complement protein of the binding moiety; and
vii) 70% collectin of the binding moiety, 20% opsonin of the binding moiety and 10% lectin of the binding moiety.

Preferably, preparing the EBN mixture comprises washing the mixture, and filtering the washed mixture.

More preferably, the washing step comprises exposing the mixture to a first enzyme solution, and soaking the mixture and the first enzyme solution in water. For example, the exposing step is done at ambient temperatures for about 5 minutes, and the soaking step for a further 5 minutes. Ambient or room temperature refers to a temperature in the range of 20 to 30° C. Even more preferably, the first enzyme solution comprises a nitrite reductase. In an embodiment, the water is obtained from a reverse osmosis process. More preferably, the washing step comprises washing the mixture in oxygenated water for about 10 minutes followed by a drying period for about 12 hours at 70° C.

Preferably, preparing the EBN mixture comprises dipping the mixture in oil prior to the contacting step, in particular after the mixture has been washed. The oil should be a food oil, i.e. an oil that is edible like a vegetable oil. The presence of the oil may facilitate the contacting step by ensuring that the mixture is surrounded by the oil to increase the affinity of the binding moiety and the target molecules. It is believed that the presence of the oil makes the mixture more lipid permissible and compatible with the target molecules which are often associated with the cell membrane, a predominantly lipid structure.

Preferably, preparing the EBN mixture comprises sterilising the washed EBN or EBN mixture prior to the contacting step, optionally at 121° C. for at least 10 minutes, for example about 10 to 20 minutes.

Preferably, the contacting step is carried out in the presence of ascorbic acid and gold nanoparticles. The ascorbic acid provide anti-oxidant properties, while the gold nanoparticles provide a stable non-reactive environment. Individually or in combination, the ascorbic acid and gold nanoparticles maintain and preserves the integrity of the extract mixture with minimised or no change to the target molecules.

Preferably, the contacting step is carried out at between 4° C. to 37° C. for at least 20 minutes. For example, the contacting step is carried out at between 25° C. to 37° C. for about 20 to 120 minutes.

Preferably, the method further comprises hydrolysing the bounded molecules with an acidic solution.

Preferably, isolating the molecule comprises separating the at least one binding moiety and bounded molecules from the mixture; releasing the bounded molecules; and obtaining the released molecules by dialysis.

Preferably, the method further comprises treating the dialysed molecule with a second enzyme solution comprising a vegetable protease and/or a fruit protease.

Preferably, the method comprises at least one of the following conditions:

(a) a concentration of the second enzyme solution is from about 10 μg/ml to 100 μg/ml; and
(b) treating of the isolated molecule with the second enzyme solution is carried out at 45° C. for 60 minutes at pH 6.5 to 9.0, and denaturing the second enzyme solution, i.e. only the enzymes in the second enzyme solution but not the target molecules.

Preferably, the method further comprises drying the molecules. The drying should be done after the molecules have been isolated, and is typically by freeze drying to preserve the quality and properties of the molecules.

In a second aspect of the invention, there is a bird's nest extract obtainable from the methods of the first aspect. In an embodiment, the bird's nest extract may further comprise an extract from seaweed and/or hasma.

In a third aspect of the invention, there is a bird's nest extract comprising a plurality of molecules selected from at least two groups comprising: opsonins, complement proteins, lectins, ficolins, collectins, and pentraxins. In an embodiment, the bird's nest extract may further comprise an extract from seaweed and/or hasma.

Preferably, the plurality of molecules is any one selected from:

i) lectins and opsonins;
ii) lectins, complement proteins, opsonins, ficolins, collectins, and pentraxins;
iii) lectins, complement proteins, and opsonins;
iv) opsonins and pentraxins;
v) ficolins, collectins, and pentraxins;
vi) complement proteins, ficolins, and collectins; and
vii) lectins, opsonins, and collectins.

More preferably, the plurality of molecules is any one selected from:

i) 50% to 90% of lectins, and 10% to 50% of opsonins;
ii) 10% to 30% of lectins, 10% to 30% of complement proteins, 10% to 30% of opsonins, 5% to 15% of ficolins, 5% to 15% of collectins, and 10% to 30% of pentraxins;
iii) 5% to 45% of lectins, 35% to 65% of complement proteins, and 5% to 45% of opsonins;
iv) 10% to 90% of opsonins, and 10% to 90% of pentraxins;
v) 30% to 50% of ficolins, 10% to 50% of collectins, and 10% to 50% of pentraxins;
vi) 55% to 85% of complement proteins, 5% to 15% of ficolins, and 10% to 30% of collectins; and
vii) 5% to 15% of lectins, 10% to 30% of opsonins, and 55% to 85% of collectins.

The percentage provided for each type of molecule is the percentage weight of each type of molecule relative to the total weight of the types of molecules present.

More preferably, the plurality of molecules is any one selected from:

i) 70% of lectins, and 30% of opsonins;
ii) 20% of lectins, 20% of complement proteins, 20% of opsonins, 10% of ficolins, 10% of collectins, and 20% of pentraxins;
iii) 25% of lectins, 50% of complement proteins, and 25% of opsonin;
iv) 50% of opsonins, and 50% of pentraxins;
v) 40% of ficolins, 30% of collectins, and 30% of pentraxins; and vi) 70% of complement proteins, 10% of ficolins, and 20% of collectins;

vii) 10% of lectins, 20% of opsonins, and 70% of collectins.

Preferably, the bird's nest extract are hydrolysed by treatment with an acid solution and/or an enzymatic solution. This breaks the extracted molecules down into smaller molecules which are more readily absorbed by the body. In an example, the hydrolysed product comprises peptides and/or free amino acids with molecular weights below 1000 Daltons, 750 Daltons, 500 Daltons, or 300 Daltons.

Preferably, the bird's next extract further comprises maltodextrin.

A composition may be provided comprising the bird's nest extract according to the second and third aspects; and a pharmaceutically-acceptable carrier, excipient or diluent. As used herein, "pharmaceutically acceptable carrier" includes any and all solvents, dispersion media, coatings, antibacterial and antifungal agents, isotonic and absorption delaying agents, and the like that are physiologically compatible.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

Preferably, the composition or formulation is a unit dosage containing a daily dose or unit, daily sub-dose or an appropriate fraction thereof, of the active ingredient. The compositions of the present invention may normally be administered orally or by any parenteral route, in the form of a pharmaceutical composition comprising the immunological concentrate, optionally in the form of a non-toxic organic, or inorganic, acid, or base, addition salt, in a pharmaceutically acceptable dosage form. Depending upon the condition, disorder and patient to be treated, as well as the route of administration, the compositions may be administered at varying doses.

In human therapy, the immunological concentrate/extract or compositions of the invention can be administered alone but will generally be administered in admixture with a suitable pharmaceutical excipient diluent or carrier selected with regard to the intended route of administration and standard pharmaceutical practice. They may be administered orally (via tablets and capsules) or parenterally, for example, intravenously, intra-arterially, intraperitoneal, intrathecal, intraventricular, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Compositions or formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. Therapeutic compositions typically must be sterile and stable under the conditions of manufacture and storage. The composition can be formulated as a solution, microemulsion, liposome, or other ordered structure suitable to high drug concentration.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the compounds of the invention will usually be from 1 mg/kg to 30 mg/kg. Thus, for example, the tablets or capsules of the compound of the invention may contain a dose of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Alternatively, the compositions of the invention can be administered in the form of a suppository or pessary, or they may be applied topically in the form of a lotion, solution, cream, ointment or dusting powder. The compositions of the invention, particularly the bird's nest extracts, may also be transdermal administered, for example, by the use of a skin patch. They may also be administered by the ocular route, particularly for treating diseases of the eye. For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyl-dodecanol, benzyl alcohol and water.

Generally, in humans, oral or topical administration of the compositions of the invention is the preferred route, being the most convenient. In circumstances where the recipient suffers from a swallowing disorder or from impairment of drug absorption after oral administration, the drug may be administered parenterally, e.g. sublingually, buccally, transmucosal or transdermal means.

In an embodiment, the bird's nest extract according to the second and third aspects may be consumed as a nutraceutical or health supplement. For example, a nutraceutical for use in modulating an immune system of a subject, the nutraceutical comprising the bird's nest extract according to the second or third aspects of the invention. The extract may be consumed as a powder, or combined with other food or drink.

In a fourth aspect of the invention, the bird's nest extract of the second and third aspects may be for use in medicine, or use in the manufacture of a medicament.

Preferably, the bird's nest extract may be for use to inhibit dengue virus replication, or for use in modulating an immune system of a subject, or for use in inducing interferon regulatory factor 3 (IRF3) phosphorylation. The subject may be any animal, preferably a mammal, more preferably a human being. More preferably, modulating the immune system is by inducing production of inflammatory cytokines, or induction of the NF-κB pathway and/or MAPK pathway. The inhibition of the dengue virus replication is preferably to prevent at least 50% of the dengue virus from replicating, at least 60% of the dengue virus from replicating, at least 70% of the dengue virus from replicating, at least 80% of the dengue virus from replicating, at least 90% of the dengue virus from replicating, at least 95% of the dengue virus from replicating, or essentially 100% of the dengue virus from replicating.

Alternatively, the bird's nest extract may be used in a method of inhibiting dengue virus replication, or modulating an immune system of a subject, or inducing interferon regulatory factor 3 (IRF3) phosphorylation, the method comprises administering the bird's nest extract of the second and third aspects to the subject, particularly in a biologically effective amount.

The methods described allows for the preparation of a bird's nest extract, and optionally containing seaweed and/or hasma, that is enriched in compounds compared to natural bird's nest. Further, the process hydrolyses the extracted products to supply the compounds in high purity and high bioavailability after consumption. The compounds extracted may be varied for different purposes by varying the extraction solution. The products isolated in this process is amenable to be delivered to the user in a variety of ways and methods to allow for effective and quick delivery of the bioactive molecules to the sites of action. The bird's nest extract may provide immune boosting effects and anti-viral properties, and may be consumed as a nutraceutical or health product. The products are a low cost source of active nutraceutical ingredients (ANI) but possess the high efficacies of active pharmaceutical ingredients (APIs).

In the Figures:

FIG. 1 shows a flow chart of a method of preparing a concentrate from bird's nest.

FIG. 2 shows the effects of a 10% mixture of a bird's nest extract (E1) on the inhibition of dengue virus (DV1) replication in macrophages. RT-PCT of DV1 negative strand (DV1neg) mRNA assayed 72 hours after DV1 infection. GAPDH served as the loading control.

FIG. 3 shows the effects of a 10% mixture of a bird's nest extract (E2) on macrophages. The figure shows that E2 can elicit the production of IFN-β and other inflammatory cytokines in macrophages. Panels A-E shows the qPCR results of macrophages after treatment with E2, with Poly(I:C) and LPS of 2 strains (0111:B4 and 055:B5) as positive controls. Boxes highlight the induction of various cytokine genes expression by E2.

FIG. 4 shows the western blot analysis of EBN-induced macrophages. Panel A shows the absence of pIRF3 band in 10% mixture of a negative control (SF) lane. Panel B shows the presence of pIRF3 band in 10% mixture of a bird's nest extract (E3) lane.

Figure 7:
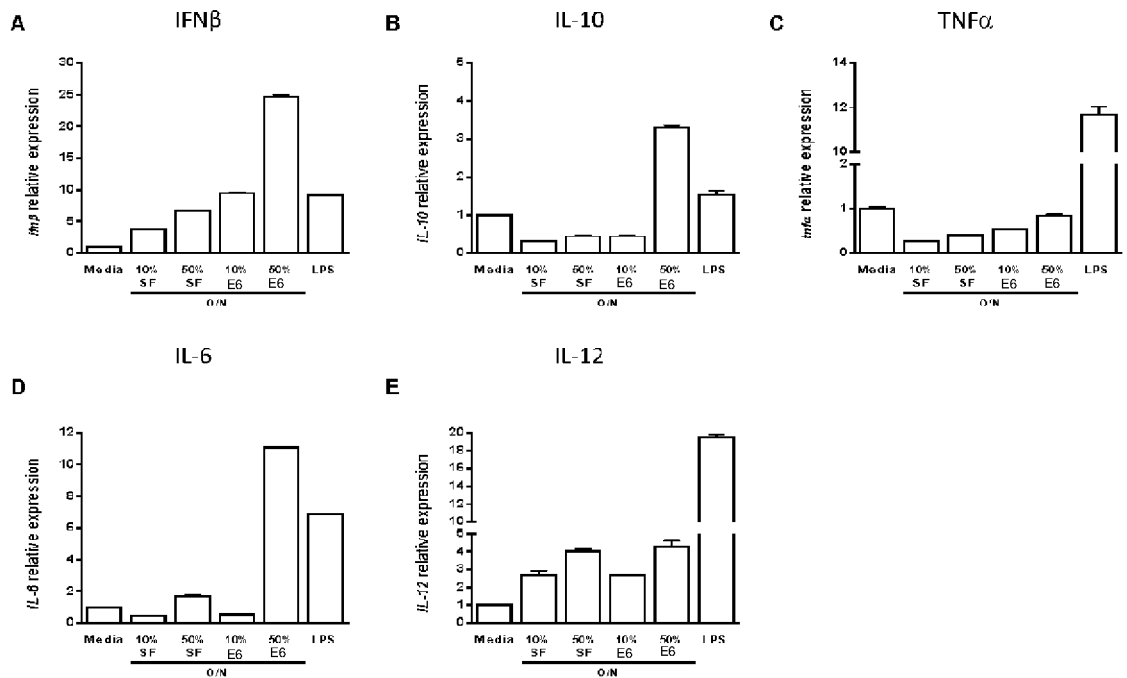

FIG. 7 shows the dose-dependent effects on B cells for cytokine production. The relative expression of cytokines in 10% and 50% mixture of edible bird's nest extract (E6) induced B lymphocytes harvested overnight. Panel A shows IFNβ, Panel B shows IL-10, Panel C shows TNFα, Panel D shows IL-6 and Panel E shows IL-12.

Figure 8:
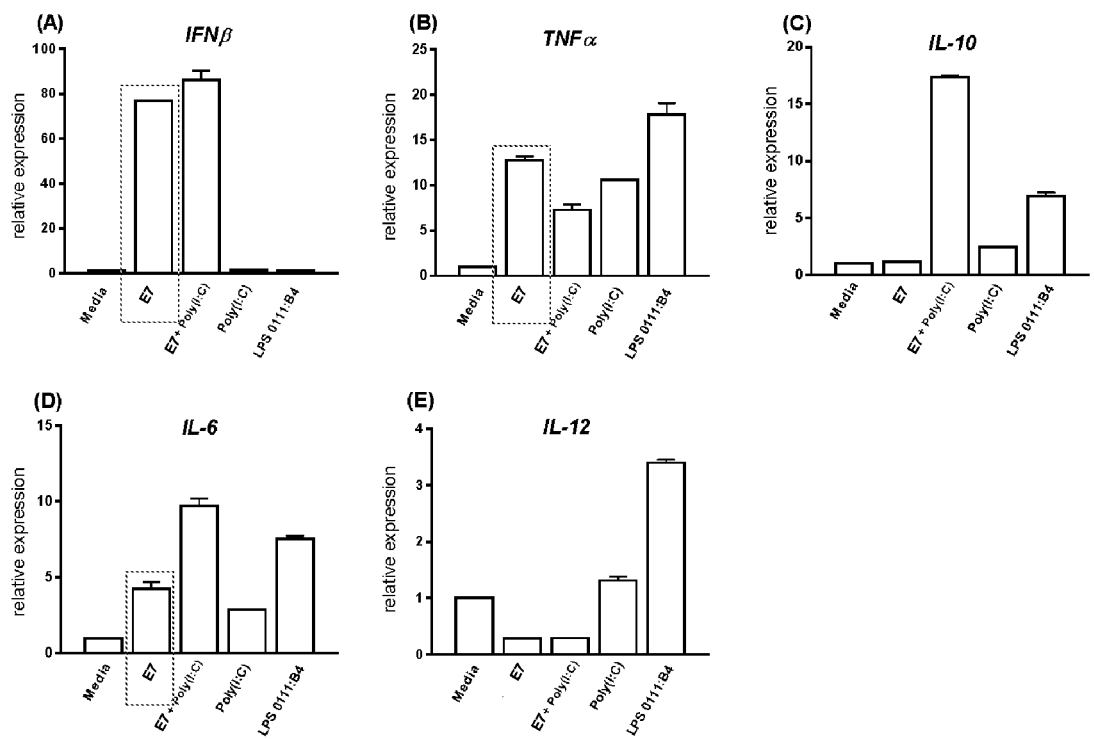

FIG. 8 shows the qPCR results of B lymphocytes after treatment with edible bird's nest extract (E7). Actin was used as the endogenous control where all gene expressions were normalised to. Expression of target genes were compared to Media with Poly(I:C), and LPS (0111:B4) as positive controls.

Figure 9:
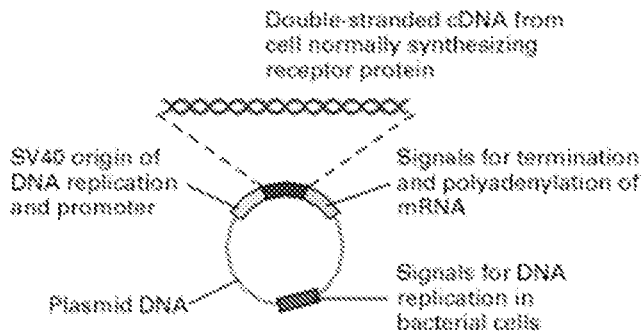
Figure 9:
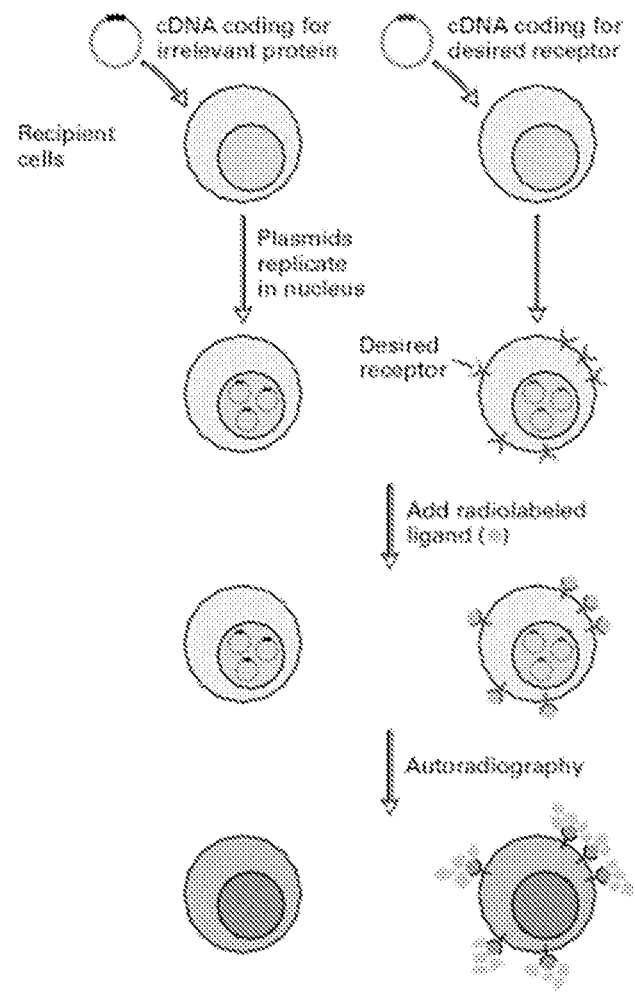

FIG. 9 shows the identification and isolation of a cDNA encoding a desired cell-surface receptor by plasmid expression cloning.

DETAILED DESCRIPTION

Unless defined otherwise, all technical and scientific terms used herein have the meaning commonly understood by a person skilled in the art to which this invention belongs.

The terms "about", "approximately", "substantially" must be read with reference to the context of the application as a whole, and have regard to the meaning a particular technical term qualified by such a word usually has in the field concerned. For example, it may be understood that a certain parameter, function, effect, or result can be performed or obtained within a certain tolerance, and the skilled person in the relevant technical field knows how to obtain the tolerance of such term.

In the following description, numerous specific details are set forth in order to provide a thorough understanding of various illustrative embodiments of the invention. It will be understood, however, to one skilled in the art, that embodiments of the invention may be practiced without some or all of these specific details. It is understood that the terminology used herein is for the purpose of describing particular embodiments only, and is not intended to limit the scope of the invention. In the drawings, like reference numerals refer to same or similar functionalities or features throughout the several views.

The human immune system protects the body from foreign organisms, and comprise an innate immune system and an adaptive immune system. The innate immune system provides immediate defence against infection, while the adaptive immune system provides a long-lasting immunity against specific foreign organisms. Parkin and Cohen (Lancet 2001, 357, 1777-1789) provided an overview of the immune system and the main components in the human body.

Major functions of the innate immune system includes recruiting immune cells to infection sites through the production of chemical factors including cytokines and to promote removal of the foreign organisms; activation of the complement cascade; and activation of the adaptive immune system.

An opsonin is any molecule that enhances phagocytosis, and includes antibodies, complement proteins, and circulating proteins (for example pentraxins, collectins and ficolins). An opsonin typically marks an antigen for an immune response or mark dead cells for recycling. Most, if not all, cell membranes maintain a non-zero transmembrane potential and makes it difficult for two cells to come together. Opsonins generally work by binding to their target cells and enhance phagocytosis, i.e. the opsonin serve as a linker. The complement system is a part of the immune system that enhances the ability of antibodies and phagocytic cells to clear microbes and damaged cells from organisms. The complement system comprises a number of complement proteins which circulate in the blood as inactive precursors and are activated by biochemical pathways. Pentraxins, collectins, and ficolins are soluble innate immune pattern-recognition proteins which identify non-self or altered-self molecular patterns on the surfaces of dying cells and promotes the programmed cell death (e.g. apoptosis) and the clearance of dying cells and cellular material by macrophages and other phagocytic cells. As defined above, the term "opsonin" in the context of the invention excludes complement proteins, lectins, ficolins, collectins and pentraxins.

Lectins are carbohydrate-binding proteins and perform recognition on the cellular and molecular level. Within the animal lectins, C-type lectins are the most abundant and are grouped into three major families: selectins, collectins and endocytic lectins. Collectins are believed to be involved in the pattern recognition of respiratory viruses and pathogenic bacteria. Examples include the collagenous lectins such as mannose binding proteins (MBP), pulmonary surfactant SP-A and SP-D and conglutinin. MBP is an example of a protective collectin that is able to bind oligomannose residues of bacterial and fungal cell surface oligosaccharides. MBP is also able to active the classical and the alternative complement pathways. Another endogenous collectin is a mannose receptor and is expressed on macrophage and dendritic cell surfaces, and are able to recognise and bind bacteria. As defined above, the term "lectin" in the context of the invention excludes ficolins and collectins, i.e. lectins other than ficolins and collectins.

Figure 1:
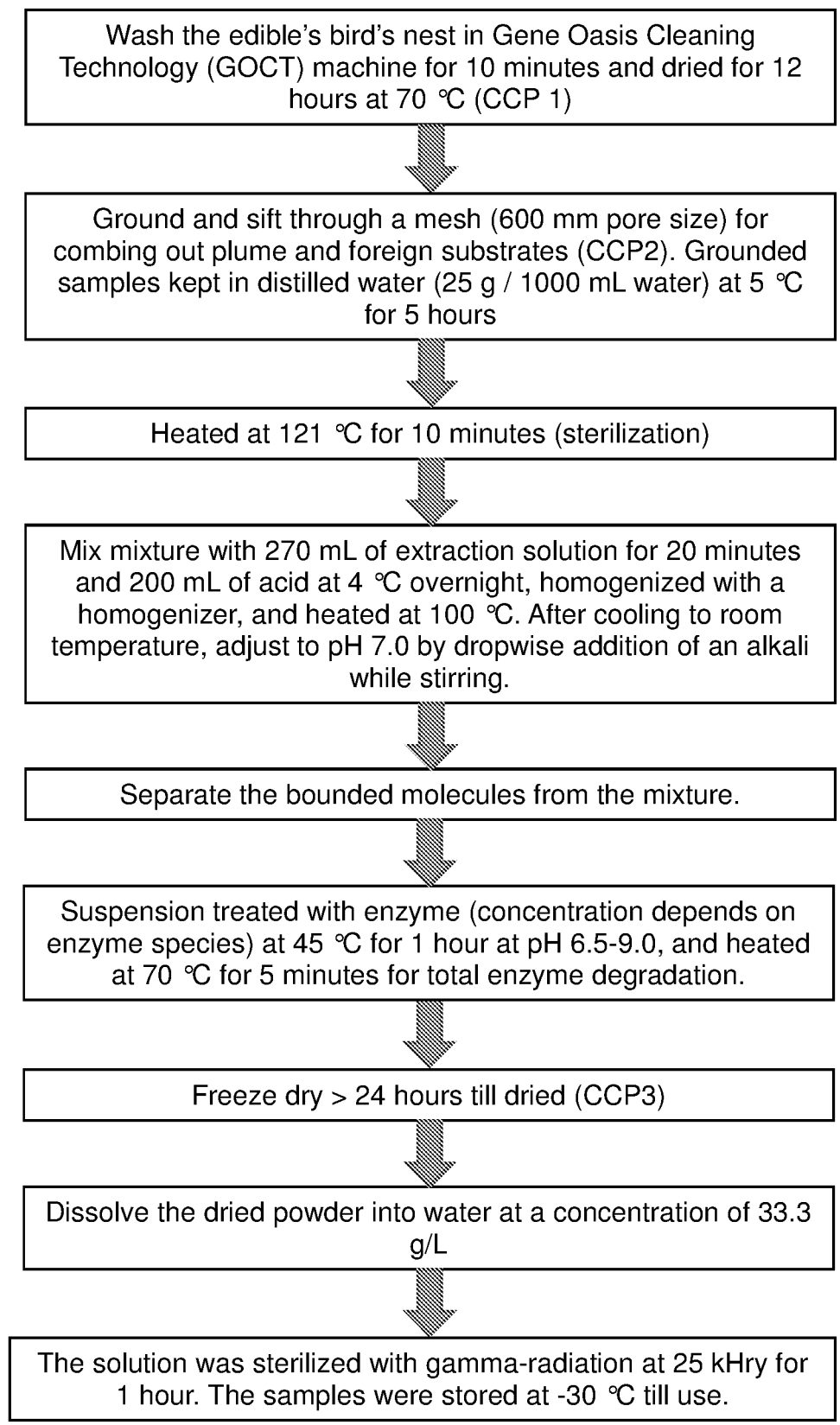

FIG. 1 shows the method to extract and isolate the bioactive molecules of interest from edible bird's nest (EBN):
  (a) cleaning EBN to remove contaminants;
  (b) grounding the cleaned EBN and sifting through a mesh;
  (c) placing the EBN powder in water to provide an EBN mixture; hasma and/or seaweed may optionally be cleaned and added into the EBN mixture as well;
  (d) sterilising the EBN or EBN mixture;
  (e) dipping the EBN or EBN mixture into oil;
  (f) treating the EBN mixture with an extraction solution comprising at least one binding moiety, the binding moiety being selected from the group comprising an opsonin binding moiety, a complement protein binding moiety, a lectin binding moiety, a ficolin binding moiety, a collectin binding moiety, and a pentraxin binding moiety;
  (g) hydrolysing the bounded molecules partially with an acidic solution;
  (h) separating the binding moiety and bioactive molecules from the EBN mixture;
  (i) releasing the bounded molecules by addition of peptides of large molecular weight;
  (j) obtaining the released bioactive molecules via dialysis;
  (k) treating the isolated fraction from dialysis with a second enzymatic solution to further break down the bioactive molecules;
  (l) denaturing and removing the enzymes of the second enzymatic solution;
  (m) drying the isolated fraction to obtain a solid product.

Certain steps described may be omitted, or performed in a different order. For example, steps (a)-(e), individually or in combination, may be considered as steps in preparing the EBN mixture for treating (or contacting) with the extraction solution. Hydrolysis of the target molecules is beneficial to maximise their biological effects. The time and temperature of the process may be varied to determine optimal parameters depending on the enzyme, binding moiety, and bioactive molecules being extracted.

The crude EBN (1 piece is approximately 10 to 50 g) is cleaned by soaking in water to remove nitrites, mites and other contaminants. The other possible contaminants that are removed may include heavy metals, bleach and other minute debris, including stains.

An effective method to remove the nitrites is to use a solution containing nitrite reductase enzymes from fruits, plants and soil. Additionally, the solution may contain another enzyme to inactivate any accompanying bacteria that produce the nitrite. To remove mites, a solution containing special fruit proteinases are used. Such examples include any such protease from papaya (papain), kiwifruit (actinidin), pineapple (bromelain), fig (ficin) etc. These proteases may be used in any suitable concentration that will allow for the inactivation of the bacteria.

The EBN mixture was treated sequentially with each enzymatic solution for at least 5 minutes from room temperature to 40° C. Nanobubbling of the resultant suspension of EBN in the enzymatic solution will cause the degraded cellular debris to float to the surface of the water where it can be easily removed. The enzymatic solution is subsequently removed from the solid EBN. The solid EBN can be further washed to remove any residual enzymes and contaminants. The cleaned EBN is dried to remove excess water, preferably at 70° C. for 12 h.

The cleaned EBN is grounded and sifted through a mesh. The size of the mesh should be sufficient to remove any large impurities left, preferably in a size of 200 to 700 μm. Most preferably the mesh size is 600 μm.

The EBN powder is placed in water, preferably distilled or deionised water, at 5° C. for 5 hours. A suitable concentration is 25 g of EBN in 1000 mL of water. The mixture may be further sterilised at 121° C. for 10 to 20 minutes if desired. Hasma and/or seaweed may also be cleaned as above and soaked in the mixture with the EBN. Alternatively, the hasma and/or seaweed may be prepared separately and added to the EBN mixture. Subsequently, the EBN mixture is dipped into oil to enhance the binding in the subsequent treatment with the binding moiety through enhanced interaction and affinity of the binding moiety and the bioactive molecules.

The EBN mixture is treated with an aqueous solution containing at least one binding moiety in a temperature range from 4 to 37° C. for at least 20 minutes. With a temperature of 25 to 37° C., 20 to 120 minutes suffice, but could be kept longer overnight at a lower temperature. With a temperature of 4° C., the mixture of antibody and EBN is kept for at least 9 hours. Generally, the lower the temperature the longer the time required for the binding moiety solution to completely bind to the targeted compounds. The binding moiety is selected from the group comprising an opsonin binding moiety, a complement protein binding moiety, a lectin binding moiety, a ficolin binding moiety, a collectin binding moiety, and a pentraxin binding moiety. In an embodiment, the contacting or mixing step of the EBN mixture and binding moiety is carried out in the presence of ascorbic acid and/or gold nanoparticles. The ascorbic acid provides anti-oxidant properties and prevents or minimises the degradation of the bioactive molecules, for example from reactive oxygen species. The gold nanoparticles provide a stable and non-reactive environment which enhances the binding of the target molecules and binding moiety. The at least one binding moiety present in the extraction solution will bind to the targeted molecule and allow the bounded molecule to be extracted out of the EBN mixture.

Examples of Binding Moieties

An example of an opsonin binding moiety protein is GP-340, a putative opsonin receptor for lung surfactant protein D. The protein has the following sequence (SEQ ID No. 1) with a molecular weight of 260.79 kDa:

```
   1 mgistvilem cllwgqvlst ggwiprttdy aslipsevpl dqtvaegspf psestlesta
  61 aegspisles tlestvaegs lipsestles tvaegsdsgl alrlvngdgr cqgrveilyr
 121 gswgtvcdds wdtndanvvc rqlgcgwams apgnawfgqg sgpialddvr csghesylws
 181 cphngwlshn cghgedagvi csaaqpqstl rpeswpvris ppvptegses slalrlvngg
 241 drcrgrvevl yrgswgtvcd dywdtndanv vcrqlgcgwa msapgnaqfg qgsgpivldd
 301 vrcsghesyl wscphngwlt hncghsedag vicsapqsrp tpspdtwpts hastagpess
 361 lalrlvnggd rcqgrvevly rgswgtvcdd swdtsdanvv crqlgcgwat sapgnarfgq
 421 gsgpivlddv rcsgyesylw scphngwlsh ncqhsedagv icsaahswst pspdtlptit
 481 lpastvgses slalrlvngg drcqgrvevl yrgswgtvcd dswdtndanv vcrqlgcgwa
 541 mlapgnarfg qgsgpivldd vrcsgnesyl wscphngwls hncghsedag vicsgpessl
 601 alrlvnggdr cqgrvevlyr gswgtvcdds wdtndanvvc rqlgcgwams apgnarfgqg
 661 sgpivlddvr csghesylws cpnngwlshn cghhedagvi csaaqsrstp rpdtlstitl
 721 ppstvgsess ltlrlvngsd rcqgrvevly rgswgtvcdd swdtndanvv crqlgcgwam
 781 sapgnarfgq gsgpivlddv rcsghesylw scphngwlsh ncghhedagv icsysqsrpt
 841 pspdtwptsh astagsessl alrlvnggdr cqgrvevlyr gswgtvcdds wdtsdanvvc
 901 rqlgcgwats apgnarfgqg sgpivlddvr csgyesylws cphngwlshn cqhsedagvi
 961 csaahswstp spdtlptitl pastvgsess lalrlvnggd rcqgrvevly qgswgtvcdd
1021 swdtndanvv crqpgcgwam sapgnarfgq gsgpivlddv rcsghesypw scphngwlsh
1081 ncghsedagv icsasqsrpt pspdtwptsh astagsessl alrlvnggdr cqgrvevlyr
1141 gswgtvcddy wdtndanvvc rqlgcgwams apgnarfgqg sgpivlddvr csghesylws
1201 cphngwlshn cghhedagvi csasqsqptp spdtwptsha stagsessla lrlvnggdrc
1261 qgrvevlyrg swgtvcddyw dtndanvvcr qlgcgwatsa pgnarfgqgs gpivlddvrc
1321 sghesylwsc phngwlshnc ghhedagvic sasqsqptps pdtwptshas tagsesslal
1381 rlvnggdrcq grvevlyrgs wgtvcddywd tndanvvcrq lgcgwatsap gnarfgqgsg
1441 pivlddvrcs ghesylwscp hngwlshncg hhedagvics asqsqptpsp dtwptsrast
1501 agsestlalr lvnggdrcrg rvevlyqgsw gtvcddywdt ndanvvcrql gcgwamsapg
1561 naqfgqgsgp ivlddvrcsg hesylwscph ngwlshncgh hedagvicsa aqsqstprpd
1621 twlttnlpal tvgsesslal rlvnggdrcr grvevlyrgs wgtvcddswd tndanvvcrq
1681 lgcgwamsap gnarfgqgsg pivlddvrcs gnesylwscp hkgwlthncg hhedagvics
1741 atqinsttd wwhpttttta rpssncggfl fyasgtfssp sypayypnna kcvweievns
```

```
1801 gyrinlgfsn lkleahhncs fdyveifdgs lnsslllgki cndtrqifts synrmtihfr 1861 sdisfqntgf lawynsfpsd atlrlvnlns syglcagrve iyhggtwgtv cddswtiqea 1921 evvcrqlgcg raysalgnay fgsgsgpitl ddvecsgtes tlwqcrnrgw fshncnhred 1981 agvicsgnhl stpapflnit rpntdyscgg flsqpsgdfs spfypgnypn nakcvwdiev 2041 qnnyrvtvif rdvqleggcn ydyievfdgp yrsspliary cdgargsfts ssnfmsirfi 2101 sdhsitrrgf raeyysspsn dstnllclpn hmqasysrsy lqslgfsasd lvistwngyy 2161 ecrpqitpnl viftipysgc gtfkqadndt idysnfltaa vsggiikrrt dlrihvscrm 2221 lqntwvdtmy iandtihvan ntiqveevqy gnfdvnisfy tsssflypvt srpyyvdlnq 2281 dlyvqaeilh sdavltlfvd tcvaspysnd ftsltydlir sgcvrddtyg pysspslria 2341 rfrfrafhfl nrfpsvylrc kmvvcraydp ssrcyrgcvl rskrdvgsyq ekvdvvlgpi 2401 qlqtpprree epr
```

An example of a complement protein binding moiety [20] protein is the complement receptor type 2 isoform 1 precursor [Homo sapiens]. The protein has the following sequence (SEQ ID No. 2) with a molecular weight of 119.18 kDa:

```
   1 mgaagllgvf lalvapgvlg iscgspppil ngrisyystp iavgtvirys csgtfrlige 61 ksllcitkdk vdgtwdkpap kceyfnkyss cpepivpggy kirgstpyrh gdsvtfackt 121 nfsmngnksv wcqannmwgp trlptcvsvf plecpalpmi hnghhtsenv gsiapglsvt 181 yscesgyllv gekiinclss gkwsavpptc eearckslgr fpngkvkepp ilrvgvtanf 241 fcdegyrlqg ppssrcviag qgvawtkmpv ceeifcpspp pilngrhign slanvsygsi 301 vtytcdpdpe egvnfilige stlrctvdsq ktgtwsgpap rcelstsavq cphpqilrgr 361 mvsgqkdryt yndtvifacm fgftlkgskq ircnaqgtwe psapvcekec qappnilngq 421 kedrhmvrfd pgtsikyscn pgyvlvgees iqctsegvwt ppvpqckvaa ceatgrqllt 481 kpqhqfvrpd vnsscgegyk lsgsvyqecq gtipwfmeir lckeitcppp pviyngahtg 541 ssledfpygt tvtytcnpgp ergvefslig estirctsnd qergtwsgpa plcklsllav 601 qcshvhiang ykisgkeapy fyndtvtfkc ysgftlkgss qirckadntw dpeipvcekg 661 cqsppglhhg rhtggntvff vsgmtvdytc dpgyllvgnk sihcmpsgnw spsaprceet 721 cqhvrqslqe lpagsrvelv ntscqdgyql tghayqmcqd aengiwfkki plckvihchp 781 ppvivngkht gmmaenflyg nevsyecdqg fyllgekklq crsdskghgs wsgpspqclr 841 sppvtrcpnp evkhgyklnk thsayshndi vyvdcnpgfi mngsrvirch tdntwvpgvp 901 tcikkafigc ppppktpngn htggniarfs pgmsilyscd qgyllvgeal llcthegtws 961 qpaphckevn csspadmdgi qkgleprkmy qygavvtlec edgymlegsp qsqcqsdhqw 1021 npplavcrsr slapvlcgia aglilltfli vitlyviskh rarnyytdts qkeafhlear 1081 evysvdpynp as
```

An example of a lectin binding moiety protein is the c Killer cell lectin-like receptor subfamily B member 1. The protein has the following sequence (SEQ ID No. 3) with a molecular weight of 25.42 kDa:

```
  1 mdqqaiyael nlptdsgpes sspsslprdv cqgspwhqfa lklscagiil lvlvvtglsv 61 svtsliqkss iekcsvdiqq srnktterpg llncpiywqq lrekcllfsh tvnpwnnsla
```

```
121 dcstkessll lirdkdelih tqnlirdkai lfwiglnfsl seknwkwing sflnsndlei 181 rgdakensci sisqtsvyse ycsteirwic qkeltpvrnk vypds
```

An example of a ficolin binding moiety protein has the following sequence (SEQ ID No. 4) with a molecular weight of 35.08 kDa:

```
  1 melsgatmar glavllvlfl hiknlpaqaa dtcpevkvvg legsdkltil rgcpglpgap 61 gpkgeagvig ergerglpga pgkagpvgpk gdrgekgmrg ekgdagqsqs catgprnckd 121 lldrgyflsg whtiylpdcr pltvlcdmdt dgggwtvfqr rmdgsvdfyr dwaaykqgfg 181 sqlgefwlgn dnihaltaqg sselrvdlvd fegnhqfaky ksfkvadeae kyklvlgafv 241 ggsagnsltg hnnnffstkd qdndvsssnc aekfqgawwy adchasnlng lylmgphesy 301 anginwsaak gykysykvse mkvrpa
```

An example of a collectin binding moiety protein is Collectin-12. The protein has the following sequence (SEQ ID No. 5) with a molecular weight of 81.53 kDa:

```
  1 mkddfaeeee vqsfgykrfg iqegtqctkc knnwalkfsi illyilcall titvailgyk 61 vvekmdnvtg gmetsrqtyd dkltavesdl kklgdqtgkk aistnselst frsdildlrq 121 qlreitekts knkdtleklq asgdalvdrq sqlketlenn sflittvnkt lqayngyvtn 181 lqqdtsvlqg nlqnqmyshn vvimnlnnln ltqvqqrnli tnlqrsvddt sqaiqriknd 241 fqnlqqvflq akkdtdwlke kvqslqtlaa nnsalakann dtledmnsql nsftgqmeni 301 ttisqaneqn lkdlqdlhkd aenrtaikfn qleerfqlfe tdivniisni sytahhlrtl 361 tsnlnevrtt ctdtltkhtd dltslnntla nirldsyslr mqqdlmrsrl dtevanlsvi 421 meemklvdsk hgqliknfti lqgppgprgp rgdrgsqgpp gptgnkgqkg ekgepgppgp 481 agergpigpa gppgerggkg skgsqgpkgs rgspgkpgpq gssgdpgppg ppgkeglpgp 541 qgppgfqglq gtvgepgvpg prglpglpgv pgmpgpkgpp gppgpsgavv plalqneptp 601 apedngcpph wknftdkcyy fsvekeifed aklfcedkss hlvfintree qqwikkqmvg 661 reshwigltd serenewkwl dgtspdyknw kagqpdnwgh ghgpgedcag liyagqwndf 721 qcedvnnfic ekdretvlss al
```

An example of a pentraxin binding moiety protein is the neuronal pentraxin receptor (Homo sapiens). The protein has the following sequence (SEQ ID No. 6) with a molecular weight of 52.86 kDa:

```
  1 mkflavllaa gmlaflgavi ciiasvplaa sparalpgga dnasvasgaa aspgpqrsls 61 alhgaggsag ppalpgapaa sahplppgpl fsrflctpla aacpsgaqqg daagaapger 121 eellllqsta eqlrqtalqq eariradqdt ireltgklgr cesglprglq gagprrdtma 181 dgpwdspali leledavral rdridrleqe lparvnlsaa papvsavptg lhskmdqleg 241 qllaqvlale kervalshss rrqrqeveke ldvlqgrvae lehgssaysp pdafkisipi 301 rnnymyarvr kalpelyaft acmwlrsrss gtgqgtpfsy svpgqaneiv lleaghepme 361 llindkvaql plslkdngwh hiciawttrd glwsayqdge lqgsgenlaa whpikphgil 421 ilgqeqdtlg grfdatqafv gdiaqfnlwd haltpaqvlg ianctapllg nvlpwedklv 481 eafggatkaa fdvckgraka
```

Examples of Suitable Extraction Solutions that May be Used with the Above Binding Moieties Include:

Extraction solution 1: 50% to 90% of the lectin binding moiety and 10% to 50% of the opsonin binding moiety;

Extraction solution 2: 10% to 30% of the lectin binding moiety, 10% to 30% of the complement protein binding moiety, 10% to 30% of the opsonin binding moiety, 5% to 15% of the ficolin binding moiety, 5% to 15% of the collectin binding moiety, and 10% to 30% of the pentraxin binding moiety;
- Extraction solution 3: 5% to 45% of the lectin binding moiety, 35% to 65% of the complement protein binding moiety, and 5% to 45% of the opsonin binding moiety;
- Extraction solution 4: 10% to 90% of the opsonin binding moiety, and 10% to 90% of the pentraxin binding moiety;
- Extraction solution 5: 30% to 50% of the ficolin binding moiety, 10% to 50% of the collectin binding moiety, and 10% to 50% of the pentraxin binding moiety;
- Extraction solution 6: 55% to 85% of the complement protein binding moiety, 5% to 15% of the ficolin binding moiety, and 10% to 30% of the collectin binding moiety; and
- Extraction solution 7: 5% to 15% of the lectin binding moiety, 10% to 30% of the opsonin binding moiety, and 55% to 85% of the collectin binding moiety.
- Extraction solution 8: 70% of the lectin binding moiety and 30% of the opsonin binding moiety;
- Extraction solution 9: 20% of the lectin binding moiety, 20% of the complement protein binding moiety, 20% of the opsonin binding moiety, 10% of the ficolin binding moiety, 10% of the collectin binding moiety, and 20% of the pentraxin binding moiety;
- Extraction solution 10: 25% of the lectin binding moiety, 50% of the complement protein binding moiety, and 25% of the opsonin binding moiety;
- Extraction solution 11: 50% of the opsonin binding moiety, and 50% of the pentraxin binding moiety;
- Extraction solution 12: 40% of the ficolin binding moiety, 30% of the collectin binding moiety, and 30% of the pentraxin binding moiety;
- Extraction solution 13: 70% of the complement protein binding moiety, 10% of the ficolin binding moiety, and 20% of the collectin binding moiety; and
- Extraction solution 14: 10% of the lectin binding moiety, 20% of the opsonin binding moiety, and 70% of the collectin binding moiety.

The percentage provided for each binding moiety is the percentage weight of each binding moiety relative to the total weight of the binding moieties present. The binding moiety/moieties may be dissolved in any suitable solvent or used as a mixture. Examples of solvent includes water and buffer solutions.

After the contacting or mixing step, the mixture is homogenised with a homogeniser, treated with an acidic solution, and heated to 100° C. to cause partial hydrolysis of the target compounds. The acid is preferably a food acid, for example ascorbic acid, citric acid, malic acid, acetic acid, tartaric acid, fumaric acid, and lactic acid. The mixture is cooled to room temperature and neutralised to a pH of 7.

After hydrolysis, the at least one binding moiety and bounded molecules can be separated from the mixture by any of the commonly known methods. Some of these methods include physicochemical fractionation, class-specific affinity and antigen-specific affinity. Physicochemical fractionation includes differential precipitation, size-exclusion or solid-phase binding of immunoglobulins based on size, charge or other shared chemical characteristics of antibodies. Class-specific affinity includes solid-phase binding of particular antibody classes (e.g. IgG) by immobilised biological ligands that have specific affinity to immunoglobulins. Antigen-specific affinity includes using specific antigens to purify antibodies through their specific antigen-binding domains.

The bounded compounds are released from the at least one binding moiety by adding excess larger peptides. For example, the larger peptides should have a minimum molecular weight of 50 kDa, and include natural glycoaminoglycans and other proteins.

The released compounds are subsequently isolated from the added peptides, enzymes and at least one binding moiety via the use of a dialysis bag.

Alternatively, the EBN containing mixture may be sequentially treated with extraction solutions comprising a different binding moiety, and separated to extract out the desired compounds sequentially. This ensures optimal use of the EBN, seaweed and/or hasma, and avoids wastage.

The isolated/concentrated compounds can be further hydrolysed with vegetable and/or food proteases at 45° C. for 1 hour at a pH of 6.5 to 9.0. The concentration of enzymes used should be at least 10 μg/mL for effective hydrolysis, and preferably up to 100 μg/mL. Examples of suitable enzymes include corn and maize terminal proteases. The enzymes are subsequently denatured by heating the mixture at 70° C. for 5 minutes. The enzymes precipitate out at a temperature above 55° C., hence the mixture can be filtered at a temperature above 55° C. to afford the desired compounds as a solution in the filtrate.

The solution of desired compounds is dried to give the compounds as a powder. Preferably, the compounds are dried by freeze drying or spray drying. The freeze drying is carried out by cooling the solution to a temperature between −180° C. to −70° C. with liquid nitrogen or dry ice, and submitting the frozen mixture to vacuum to sublime the ice. The freeze drying can be repeated if required to give a dried powdered product.

A bird's nest concentrate or extract obtained from the process described above comprise the bioactive molecules extracted from the process described. In some embodiments, the bioactive molecules may have been broken down and may be difficult to characterise. In some embodiments, the bioactive molecules may be largely intact.

As such, the bird's nest extract comprises a plurality of molecules selected from at least two of the following groups: opsonin, a complement protein, a lectin, a ficolin, a collectin, and a pentraxin. The bird's nest extract may further include extracts from hasma and/or seaweed.

In an embodiment, the bird's nest extract comprises any one selected from:

i) the lectin and the opsonin;
ii) the lectin, the complement protein, the opsonin, the ficolin, the collectin, and the pentraxin;
iii) the lectin, the complement protein, and the opsonin;
iv) the opsonin and the pentraxin;
v) the ficolin, the collectin, and the pentraxin;
vi) the complement protein, the ficolin, and the collectin; and
vii) the lectin, the opsonin, and the collectin.

In particular, the bird's nest extract comprises any one selected from:

i) 50% to 90% of the lectin, and 10% to 50% of the opsonin ii) 10% to 30% of the lectin, 10% to 30% of the complement protein, 10% to 30% of the opsonin, 5% to 15% of the ficolin, 5% to 15% of the collectin, and 10% to 30% of the pentraxin;

iii) 5% to 45% of the lectin, 35% to 65% of the complement protein, and 5% to 45% of the opsonin;

iv) 10% to 90% of the opsonin, and 10% to 90% of the pentraxin;

v) 30% to 50% of the ficolin, 10% to 50% of the collectin, and 10% to 50% of the pentraxin;

vi) 55% to 85% of the complement protein, 5% to 15% of the ficolin, and 10% to 30% of the collectin;

viii) 5% to 15% of the lectin, 10% to 30% of the opsonin, and 55% to 85% of the collectin. The percentage given is the percentage weight of the particular bioactive molecule relative to the total weight of bioactive molecules present.

The following bird's nest extracts 1 to 7 were prepared based on the process described above using the extraction solutions 8 to 14 respectively, and are reflective of the properties possess by extracts with ranges encompassing these examples:

Extract 1 was prepared using EBN and comprises: 70% of lectins, and 30% of opsonins;

Extract 2 was prepared using EBN, hasma and seaweed, and comprises: 20% of lectins, 20% of complement proteins, 20% of opsonins, 10% of ficolins, 10% of collectins, and 20% of pentraxins;

Extract 3 was prepared using EBN and seaweed, and comprises: 25% of lectins, 50% of complement proteins, and 25% of the opsonin;

Extract 4 was prepared using EBN and seaweed and comprises: 50% of opsonins, and 50% of pentraxins;

Extract 5 was prepared using EBN and comprises: 40% of ficolins, 30% of collectins, and 30% of pentraxins;

Extract 6 was prepared using EBN and hasma, and comprises: 70% of complement proteins, 10% of ficolins, and 20% of collectins;

Extract 7 was prepared using EBN and hasma, and comprises: 10% of lectins, 20% of opsonins, and 70% of collectins.

The dried powdered product may be mixed with other additives to give a food or pharmaceutical product. Alternatively, the product may be dissolved in water along with other additives.

The dried product may be mixed with maltodextrin in various formulations as follows:

1. 75% of EBN/EBN mixture concentrate/extract product and 25% maltodextrin;
2. 50% of EBN/EBN mixture concentrate/extract product and 45% maltodextrin;
3. 50% of EBN/EBN mixture concentrate/extract product and 50% maltodextrin;
4. 30% of EBN/EBN mixture concentrate extract product and 70% maltodextrin.

It may be seen that the product comprises EBN concentrate/extract product and maltodextrin. Preferably, 30 to 75 wt. % of the EBN concentrate/extract and 25 to 70 wt. % of maltodextrin.

Bioavailability of these bioactive molecules are generally very poor due to their high water solubility. Common administration routes via topical application to the skin and joints, or oral administration is hampered by the poor permeability through the skin or hydrophobic membranes in the intestine. It is difficult for the bioactive molecules to reach the requisite sites in the body to have the desired effect. Other methods of administration are available but is generally not suitable to be administered without a health professional. The hydrolysis of the bioactive molecules partially by acidic and/or enzymatic hydrolysis may prove to be beneficial to break down the molecules into more easily absorbable compounds making the extract more beneficial.

Especially with a suitable formulation, the respective proprietary immunological concentrates can be delivered in effective and useful doses to the sites of pain and inflammation.

Formulated in lipid forms, the present concentrate/extract may be used to produce a first economical product in the market that is transdermal and is composed of safe and sustainable bioactive molecules, purified/extracted from natural but abundant supplies of EBN/EBN mixture recycled crumbs.

Extracts 1 to 7 (E1-E7) were tested on macrophages/B cells cell culture in vitro to determine their effects on the production of Type-1 IFN, cytokine production, and dengue virus replication. Macrophages/B cells in this application refer to differentiated primary macrophages/B cells derived from bone-marrow progenitor's stem cells from mouse femurs. All these features are commonly used indicators of protective immune response of macrophages/B cells in vitro.

Methods and Results of Biological Assays

1. Method of Cell Culture and Dengue Virus Replication Assays

Bone Marrrow-Derived Macrophage Culture

Bone marrow cells were obtained by injecting culture media into the femur and tibia. All cells were spun down by centrifuging 1000 rpm for 5 mins at 4° C. To eliminate erythrocytes, cells were treated with 1 ml of red blood cells lysis buffer for 5 mins by incubating on ice. The cells were washed in 10 ml culture media and collected by centrifuging at 1000 rpm for 5 mins at 4° C. Bone marrow cells were counted using haemocytometer and 106 cells were differentiated on 10 cm culture plate containing 10 ml of MCSF containing media for 6 days.

Dengue Virus Infection of Macrophages

Dengue type 1 virus (Singapore Strain S275/90, D1) was propagated in C6/36 cells. Bone marrow-derived macrophages (3×106) were seeded into each well of 6-well tissue-culture plate (NUNC). After overnight incubation, macrophages were infected with D1 at a multiplicity of infection (M01) of 1 for 2 days. For detection of negative-strand D1 RNA, total RNA was extracted from D1-infected cells using TRIzol (Invitrogen). 1 µg of total RNAs was subject to reverse transcription with primer 5'-GTGCTGCCTGTGGCTCCATC-3', and was subsequently used as a template for synthesis of a PCR fragment with the primer pair 5'-AGAACCTGTTGATT-CAACAGCACC-3' and 5'-CATGGAAGCTGTACG-CATGG-3'. For detection of GAPDH by Reverse-Transcriptase PCR, cellular cDNAs were synthesized from above total RNA with oligodT primer. GAPDH fragments were synthesized with the following primers, murine GAPDH, 5'-GACAACTTTGGCATTGTGGAA-3' and 5'-CCAG-GAAATGAGCTTGACA-3', respectively.

Figure 2:
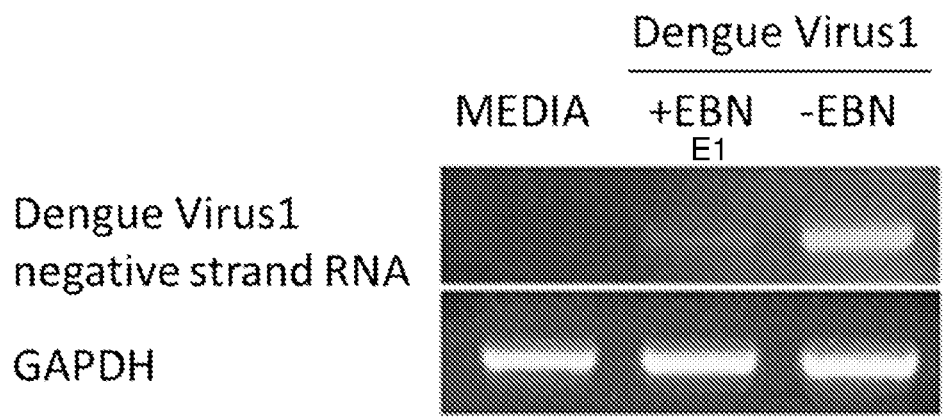

Referring to FIG. 2, it may be seen that the middle lane with the macrophages treated with Extract 1 (E1) in the above assay shows the absence or weak presence of a white band, indicating that Extract 1 restricts the replication of the dengue virus in macrophages. This may be used as a means to control the dengue virus replication.

2. Method of Cell Culture, Real-Time Genes Expression Quantitative-PCR (qPCR)

Bone Marrow-Derived Macrophage Culture

Bone marrow cells were obtained by injecting culture media into the femur and tibia. All cells were spun down by centrifuging 1000 rpm for 5 mins at 4° C. To eliminate erythrocytes, cells were treated with 1 ml of red blood cells lysis buffer for 5 mins by incubating on ice. The cells were washed in 10 ml culture media and collected by centrifuging at 1000 rpm for 5 mins at 4° C. Bone marrow cells were counted using haemocytometer and 106 cells were differentiated on 10 cm culture plate containing 10 ml of MCSF containing media for 6 days.

Quantitative Real-Time PCR

2×106 cells/ml of bone marrow macrophages were seeded onto 6 well plate in Opti-MEM (Gibco, US). Cells were stimulated with 50 μg/ml Poly(I:C) (InvivoGen, US), 1 μg/ml LPS 0111:B4 (purified from LPS 0111:B4) and 1 μg/ml LPS 055:B5 (Sigma, US) for 2 hours before RNA extraction using TRIzol (Invitrogen, US). 1 μg cDNA was synthesized from total RNA with Superscript III First Strand Synthesis System (Invitrogen, US) according to manufacturer's protocol. qPCR was performed on Applied Biosystems QuantStudio 6 Flex Real Time PCR system with the cytokine specific primers.

Figure 3:
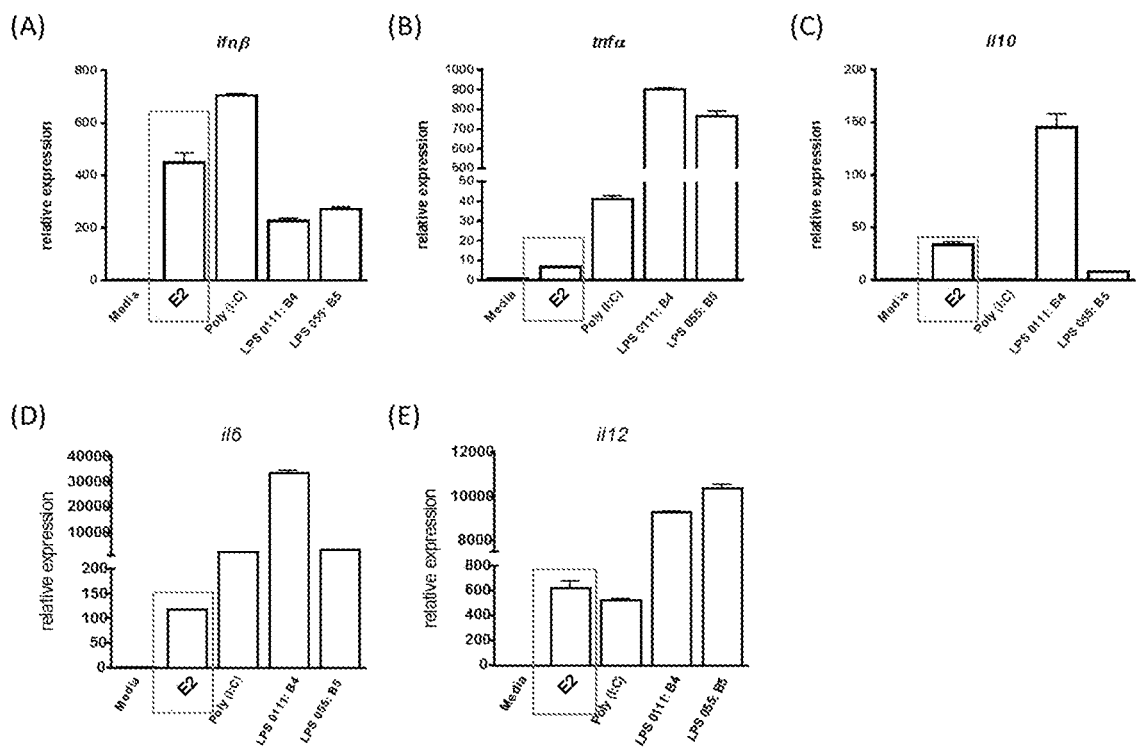

Referring to FIG. 3, it can be seen that the positive controls elicit the production of IFNβ, TNFα, IL-10, IL-6, and IL-12 to different extents. Extract 2 (E2) elicit the production of IFNβ and inflammatory cytokines in macrophages, and provide a most complete immune balancing platform whereby key immune molecules could be harvested to influence the orchestration of various pro-inflammatory and anti-inflammatory molecules to achieve a balanced state of immune system, manifested not just by macrophages but other important cells as well. The symphony of immune molecules that would produce enhanced effects of prevention of microbial infections as well as better management of cancers. Extract 2 could possibly possess anti-dengue properties as well.

3. Phosphorylation of IRF3 in Macrophages

Figure 4:
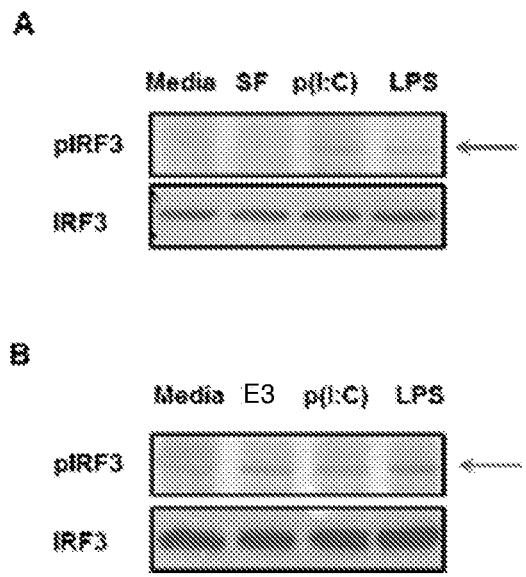

Extract 3 (E3) when applied to macrophages induce phosphorylation of IRF3 in macrophages as shown in FIG. 4 panel B. The lane marked E3 in the western bolt analysis shows the phosphorylation of IRF3 same as the positive controls poly(I:C) and LPS. Panel A of FIG. 4 shows the negative control in the SF marked lane. Activated IRF3 has been linked with enhanced anti-cancer and viral prevention properties through interaction with IRF7. Modulated properly via the adoption of the different ranges of triggering immune peptides, this might also be employed successfully in post-myocardial infarction cardioprotection.

The negative control (SF) is the edible bird's nest which had not undergo the extraction process, and may be prepared by soaking the edible bird's nest in water and made up to the same mass concentration as the extract being tested. The SF control may be prepared similarly for the other assays.

4. Induction of NF-κB and MAPK Pathway in Immune Cells

Figure 5:
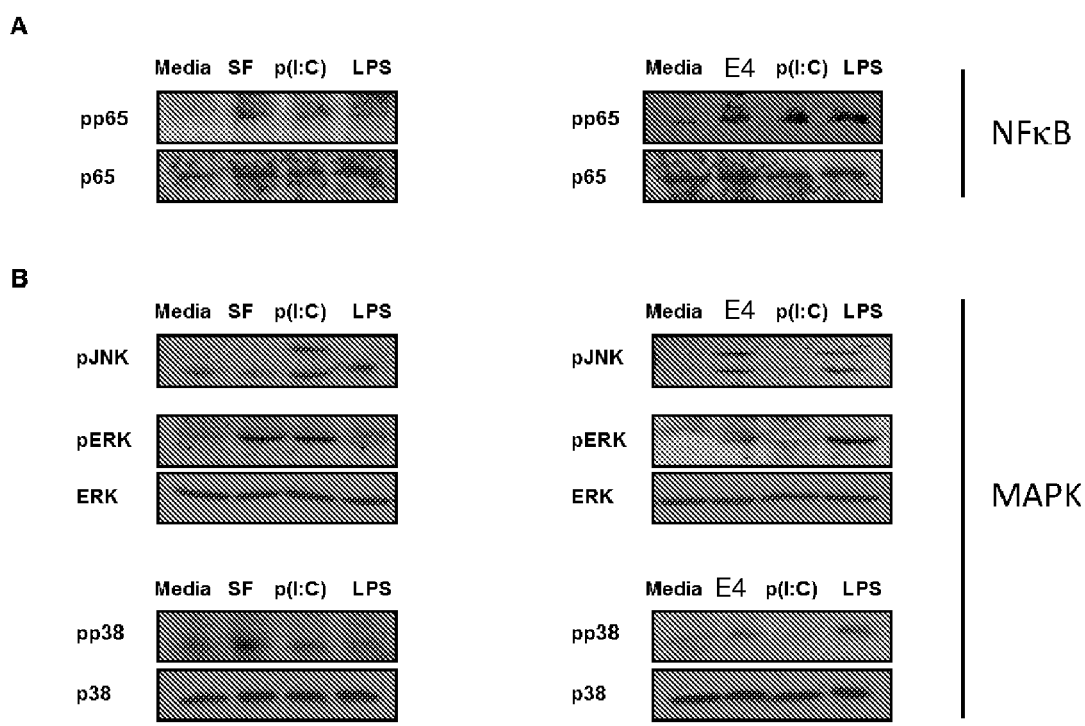
FIG. 5 shows the western bolt analysis of a 50% mixture of an edible bird's nest extract (E4) and a 50% mixture of a negative control (SF) induced macrophages on the NFκB pathway and MAPK pathway in Panels A and B respectively.

Extract 4 (E4) when applied to the immune cells elicit the induction of the NFκB and MAPK pathway in immune cells as shown in FIG. 5. It can be seen in the Western bolt analysis that the immune cells treated with Extract 4 induces phosphorylation of p65, JNK, ERK, and p38 as shown in the lanes marked with Extract 4 while those with the negative control (SF lane) do not show the phosphorylated band.

NF-κB plays a key role in regulating the immune response to infection. Incorrect regulation of NF-κB has been linked to cancer, inflammatory and autoimmune diseases, septic shock, viral infection, and improper immune development. NF-κB has also been implicated in processes of synaptic plasticity and memory.

MAPKs are involved in directing cellular responses to a diverse array of stimuli, such as mitogens, osmotic stress, heat shock and proinflammatory cytokines. They regulate cell functions including proliferation, gene expression, differentiation, mitosis, cell survival, and apoptosis.

Extract 4 may be used in enhanced management of the various forms of stress, heat shock, and septic shock.

5. Induction of B Cells to Produce Cytokines

Figure 6:
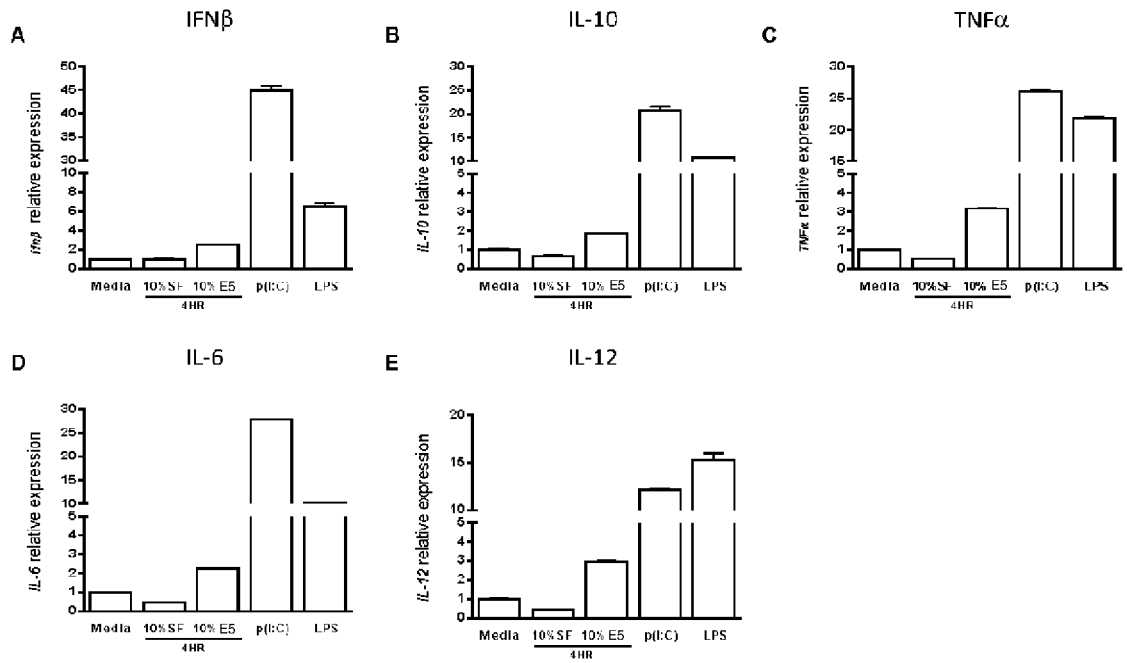
FIG. 6 shows the relative expression of cytokines in 10% mixture of edible bird's nest extract (E5) induced B lymphocytes at a time point of 4 hours. Panel A shows IFNβ, Panel B shows IL-10, Panel C shows TNFα, Panel D shows IL-6 and Panel E shows IL-12.

Extract 5 (E5) could induce B cells to produce cytokines in culture as shown in FIG. 6. It can be seen in FIG. 6 that the lane marked 10% Extract 5 (10% wt. of Extract 5 in aqueous solution) shows increased production of IFNβ, TNFα, IL-10, IL-6, and IL-12 compared to the negative control (media) and 10% SF (a negative control). Although pentraxin is associated with B cells, ficolins and collectins may not be. However, the presence of the three different type of bioactive molecules could induce a wide pool of different B cells to produce a huge diversity of cytokines to cope better with the very challenging various chronic diseases such as diabetes, arthritis, multiple sclerosis, etc.

6. Dose-Dependent Effect on B Cells for Cytokine Production

Extract 6 (E6) when applied to B cells shows dose-dependent effects on B cells for cytokine production as shown in FIG. 7, in particular for IFNβ, IL-10, and IL-6. By replacing pentraxin with complement proteins, with a combination of immune peptides that may not be closely associated to B cells, dose dependent effects on B cells for cytokine production may be achieved. These dose dependent and prolonged overnight effects may be manifested using Extract 6 instead of Extract 5 above. The rationale is that since all ficolins, collectins and complement proteins are components of the non-humoral arm of innate immunity, the earlier stage of the innate immunity, their overall effects could be more sustainable as the span of operational period of this composition could be longer, since the time covered by the earlier stage could be more accounted for.

7. Selective Induction of IFNβ, TNFα, and IL-6, but not 11-10 and IL-12, in B Cells Extract 7 (E7) when applied to B cells selectively induce IFN β, TNF α, and IL-6 in B cells, but not 11-10 and IL-12, as shown in FIG. 8. The increased expression of IFNβ, TNFα, and IL-6 are marked with a box to indicate the beneficial effects of Extract 7.

The primary role of TNF is in the regulation of immune cells. TNF, being an endogenous pyrogen, is able to induce fever, apoptotic cell death, cachexia, inflammation and to inhibit tumorigenesis and viral replication and respond to sepsis via IL1 & IL6 producing cells.

Interferon beta (IFNβ) balances the expression of pro- and anti-inflammatory agents in the brain, and reduces the number of inflammatory cells that cross the blood brain barrier. Overall, therapy with interferon beta leads to a reduction of neuron inflammation. Moreover, it is also thought to increase the production of nerve growth factor and consequently improve neuronal survival.

Interleukin 6 (IL-6) is an interleukin that acts as both a pro-inflammatory cytokine and an anti-inflammatory myokine. Interleukin 6 is secreted by T cells and macrophages to stimulate immune response, e.g. during infection and after trauma, especially burns or other tissue damage leading to inflammation. IL-6 also plays a role in fighting infection. In addition, osteoblasts secrete IL-6 to stimulate osteoclast formation. Smooth muscle cells in the tunica media of many blood vessels also produce IL-6 as a pro-inflammatory cytokine. IL-6's role as an anti-inflammatory cytokine is mediated through its inhibitory effects on TNF-alpha and IL-1, and activation of IL-1ra and IL-10.

TNF, IFNβ and IL-6 together present a very novel but balanced immune modulating platform whereby there could be self-balancing of pro-inflammatory and anti-inflammatory factors. The novelty of combining the likely presence of opsonins, lectins and collectins (although they are associated peptides) in the immunological concentrate has yielded the ability of B cells to have induced expression of TNF, IFNβ and IL-6 together. When there is a balanced immune modulating platform, symptoms such as loss of weight, muscle atrophy, fatigue, weakness, significant loss of appetite, bone loss or even neurodegeneration would be alleviated. Cancer would also be less likely to occur as a result of a healthy and balanced immune system.

As can be seen from the assays and results discussed, the bird's nest Extracts 1 to 7 are able to induce various immune cells to increase production of cytokines, both pro and anti-inflammatory cytokines. This modulates the immune system as both types of cytokines are boosted balancing the cytokines present in the body. This prevents the overproduction of a particular cytokine.

The bird's nest extract whether as defined by the process or by the product itself, are suitable to be consumed as a nutraceutical or health supplement. It may potentially be usable as a medicament in certain compositions.

The process described herein allows for valuable bioactive molecules to be extracted from EBN, and provide for a cost effective and important source of immune boosters.

Whilst there has been described in the foregoing description preferred embodiments of the invention, it will be understood by those skilled in the field concerned that many variations or modifications in details of design or construction may be made without departing from the present invention.

The invention claimed is:

1. A method of preparing an extract from edible bird's nest, the method comprising:
   (a) preparing an edible bird's nest (EBN) mixture; and
   (b) contacting the mixture with an extraction solution to bind a molecule in the mixture, wherein the extraction solution comprises at least one binding moiety selected from the group consisting of an opsonin binding moiety, a complement protein binding moiety, a lectin binding moiety, a ficolin binding moiety, a collectin binding moiety, and a pentraxin binding moiety.

2. The method according to claim 1, wherein the mixture further comprises seaweed and/or hasma.

3. The method according to claim 1, wherein the opsonin binding moiety has a molecular weight of 10 kDa to 750 kDa and comprises SEQ ID No. 1.

4. The method according to claim 1, wherein the complement protein binding moiety has a molecular weight of 20 kDa to 7000 kDa and comprises SEQ ID No. 2.

5. The method according to claim 1, wherein the lectin binding moiety has a molecular weight of 20 kDa to 1000 kDa and comprises SEQ ID No. 3.

6. The method according to claim 1, wherein the ficolin binding moiety has a molecular weight of 15 kDa to 900 kDa and comprises SEQ ID No. 4.

7. The method according to claim 1, wherein the collectin binding moiety has a molecular weight of 15 kDa to 900 kDa and comprises SEQ ID No. 5.

8. The method according to claim 1, wherein the pentraxin binding moiety has a molecular weight of 20 kDa to 1000 kDa and comprises SEQ ID No. 6.

9. The method according to claim 1, wherein the extraction solution comprises any one selected from the group consisting of:
   i) 70% lectin and 30% opsonin;
   ii) 20% lectin, 20% complement protein, 20% opsonin, 20% pentraxin, 10% ficolin, and 10% collectin;
   iii) 50% complement protein, 25% lectin and 25% opsonin;
   iv) 50% opsonin and 50% pentraxin;
   v) 40% ficolin, 30% collectin and 30% pentraxin;
   vi) 10% ficolin, 20% collectin and 70% complement protein; and
   vii) 70% collectin, 20% opsonin and 10% lectin.

10. The method according to claim 1, wherein preparing the EBN mixture in step (a) comprises washing the mixture, wherein the washing comprises exposing the mixture to a first enzyme solution, and soaking the mixture and the first enzyme solution in water, and filtering the washed mixture.

11. The method according to claim 10, wherein the first enzyme solution comprises a nitrite reductase.

12. The method according to claim 10, wherein preparing the EBN mixture comprises dipping the EBN mixture in oil prior to the contacting step (b).

13. The method according to claim 10, wherein preparing the EBN mixture further comprises sterilising the washed EBN mixture prior to the contacting step (b).

14. The method according to claim 1, wherein the contacting step (b) is carried out in the presence of an ascorbic acid and a gold nanoparticle, at between 4° C. to 37° C. for at least 20 minutes.

15. The method according to claim 1, further comprising hydrolysing the bound molecules with an acidic solution.

16. The method according to claim 1, further comprising separating the at least one binding moiety and bound molecules from the mixture; releasing the bound molecules; and obtaining the released molecules by dialysis.

17. The method according to claim 16, further comprising treating the dialysed molecules with a second enzyme solution comprising a vegetable protease and/or a fruit protease with at least one of the following conditions:
   (a) a concentration of the second enzyme solution is from about 10 µg/ml to about 100 µg/ml; and/or
   (b) treating of the isolated molecule with the second enzyme solution is carried out at 45° C. for 60 minutes at pH 6.5 to 9.0, and then denaturing the second enzyme solution.

* * * * *